(12) United States Patent
Edic et al.

(10) Patent No.: US 7,333,648 B2
(45) Date of Patent: Feb. 19, 2008

(54) FEATURE QUANTIFICATION FROM MULTIDIMENSIONAL IMAGE DATA

(75) Inventors: Peter Michael Edic, Albany, NY (US); Mehmet Yavuz, Irving, TX (US); Ahmad Nadeem Ishaque, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 623 days.

(21) Appl. No.: 10/862,101

(22) Filed: Jun. 4, 2004

(65) Prior Publication Data

US 2004/0223636 A1   Nov. 11, 2004

Related U.S. Application Data

(63) Continuation of application No. 09/648,958, filed on Aug. 25, 2000, now abandoned.

(60) Provisional application No. 60/197,208, filed on Apr. 14, 2000, provisional application No. 60/166,499, filed on Nov. 19, 1999.

(51) Int. Cl.
    *G06K 9/00* (2006.01)
    *G06K 9/46* (2006.01)
(52) U.S. Cl. ................ 382/131; 382/154; 382/190
(58) Field of Classification Search .......... None
    See application file for complete search history.

(56) References Cited

U.S. PATENT DOCUMENTS 5,757,877 A * 5/1998 Wilting .................. 378/8
6,301,498 B1 * 10/2001 Greenberg et al. ......... 600/425
7,149,333 B2 * 12/2006 Pieper et al. ............. 382/128

* cited by examiner

*Primary Examiner*—Bhavesh M Mehta
*Assistant Examiner*—Charles Kim
(74) *Attorney, Agent, or Firm*—Jean K. Testa; Curtis B. Brueske

(57) ABSTRACT

Techniques, hardware, and software are provided for quantification of extensional features of structures of an imaged subject from image data representing a two-dimensional or three-dimensional image. In one embodiment, stenosis in a blood vessel may be quantified from volumetric image data of the blood vessel. A profile from a selected family of profiles is fit to selected image data. An estimate of cross sectional area of the blood vessel is generated based on the fit profile. Area values may be generated along a longitudinal axis of the vessel, and a one-dimensional profile fit to the generated area values. An objective quantification of stenosis in the vessel may be obtained from the area profile. In some cases, volumetric image data representing the imaged structure may be reformatted to facilitate the quantification, when the structural feature varies along a curvilinear axis. A mask is generated for the structural feature to be quantified based on the volumetric image data. A curve representing the curvilinear axis is determined from the mask by center-finding computations, such as moment calculations, and curve fitting. Image data are generated for oblique cuts at corresponding selected orientations with respect to the curvilinear axis, based on the curve and the volumetric image data. The oblique cuts may be used for suitable further processing, such as image display or quantification.

21 Claims, 23 Drawing Sheets

FEATURE QUANTIFICATION FROM MULTIDIMENSIONAL IMAGE DATA

CROSS REFERENCE TO RELATED APPLICATIONS

This application a continuation of application Ser. No. 09/648,958, filed Aug. 25, 2000, now abandoned which parent application is related to Provisional Application U.S. Ser. No. 60/197,208, filed Apr. 14, 2000 and Provisional Application U.S. Ser. No. 60/166,499, filed Nov. 19, 1999, in the U.S. Patent and Trademark Office. The contents of the aforementioned Provisional Application are incorporated herein by reference, and the benefit of priority to the same Provisional Application is claimed under 35 U.S.C. §119(e).

BACKGROUND OF THE INVENTION

The present invention relates to quantitative analysis of image data. More specifically, the invention relates to quantification of extensional features of structures of an imaged subject from image data representing a two-dimensional or three-dimensional image. In a particular embodiment, the invention may be used for analysis of tomographic image data for quantification of stenosis in vascular structures, such as arteries.

Various imaging modalities exist for generating images that accurately represent the interiors of objects. Tomography (or computed tomography, abbreviated "CT") is a class of such modalities. Unlike direct images (such as photographic images, conventional radiographs, etc.), a tomographic image is generated by reconstructing image data from projection data. The "projection data" are data that represent properties of, for example, illuminating rays transmitted through the object along numerous non-parallel paths. Reconstruction of the projection data into image data may be carried out through an appropriate computational process for image reconstruction.

In a typical case, a relevant set of projection data will represent attenuation of illuminating rays that travel along different paths in a specific plane. Generally the plane is transverse to a specified axis through the object and intersects the axis at a corresponding axial position. In the simplest case the plane is perpendicular to the specified axis, and the reconstructed image is a two-dimensional image representing the intersection of the plane with the structural features of the object.

Such an image is "tomographic" because it is obtained from projections through the object in many different directions generally parallel to the plane of the image. Although the image must be reconstructed from the projection data, the orientation of the directions of projection ensures that the reconstructed image substantially depicts only those features of the object coincident with the specified plane. In contrast, a conventional radiographic image (whether generated by analog or digital detection) is obtained directly from a projection generally perpendicular to the image plane. The conventional radiograph therefore depicts a superposition of all the structures of the object between the source and the detection surface (e.g., the film).

More generally, as used herein, the term "tomographic image" will mean any image generated by a process of tomography. A three-dimensional image of the interior of the object is therefore a "tomographic image," also, if reconstructed from projection data. A tomographic image depicting a cross section of the object is sometimes called a tomographic "slice" image.

A slice image may be reconstructed from projection data corresponding to a particular transverse plane through the object and may represent the features of the object lying in that plane. Alternatively, using multi-planar reconstruction ("MPR"), the projection data for several different planes may be combined to generate a slice image corresponding to yet another plane transverse to all of the projection data planes. A feature common to both types of slice image, as well as to three-dimensional images, is that each data element (pixel or voxel) represents a material property (such as attenuation of the illuminating rays) at a specific point of the object.

The projection data are generated in a process that begins by illuminating the object from numerous different directions and collecting detector data representing material characteristics of the object. It is well known that tomographic imaging can be performed by illumination with any of various types of reflected or transmitted energetic rays or waves. The source of the illuminating rays or waves is often outside the object, but can also be within the object (in so-called emission tomography). Usually the image reconstruction process comprises a computationally intensive sequence of calculations to convert the projection data into image data representing an accurate and recognizable image of the object's interior.

Medical applications of tomography have become commonplace and are widely known to provide images of almost photographic detail. A trained physician can draw detailed diagnostic conclusions from a single tomographic slice image. More generally, tomographic imaging has become a useful tool in such diverse areas of application as nondestructive testing, microseismic mapping of underground geological formations, and three-dimensional imaging with electron microscopy.

In the context of medical applications, the challenges of early diagnosis and treatment of disease continue to demand improved assessment methods. For example, serious limitations have continued to exist in the available approaches for assessment of vascular disease. An example is the assessment of vascular stenosis. Vascular disease, principally in the form of atherosclerosis leading to vessel stenosis, is a leading cause of tissue infarction and ischemia.

Here, "stenosis" means an abnormal narrowing of the vessel lumen, which is the cavity that is enclosed by the vessel walls and through which the circulating blood flows. Stenosis reduces the vessel's capacity to convey blood and thus can seriously reduce perfusion in the affected organ. The most common cause of vascular stenosis is the accumulation of atherosclerotic plaques on the interior wall of the vessel.

Several imaging modalities have been available for assessing vascular disease. The standard technique for assessment of atherosclerotic stenosis is angiographic catheterization. This technique typically entails the placement of a catheter in a branch of the affected vessel, injecting a radio-opaque contrast agent while X-ray fluoroscopic images are acquired using an image intensifier or a digital detector array.

Catheterization procedures are effective but are also highly invasive. Moreover, conventional techniques for assessment by catheterization involve acquiring two dimensional (2D) projection images of the 3D vasculature. Hence the data that is acquired may be confounded by structures in the chest or by contortions of the vessels themselves.

Ultrasound imaging has been suggested for assessment of vascular stenosis. Intravascular ultrasound (IVUS) has been implemented with some success to acquire dynamic images of the affected vasculature. However, as with conventional angiographic catheterization, IVUS techniques are highly invasive. Noninvasive ultrasound techniques produce images that are affected by such variables as the probe placement between other body structures and the proximity of the probe to the vasculature of interest. These factors, and the need for a skilled operator to collect reliable data, raise important issues for reliable and repeatable assessment of vascular disease.

Both x-ray tomography (XCT) and magnetic resonance (MR) tomography have been proposed for assessment of vascular stenosis. For example, U.S. Pat. No. 5,757,877, issued to Wilting, discloses a technique for estimating stenosis in renal arteries from tomographic slice images. The technique applied therein obtains a quantitative assessment of stenosis by estimating the diameter of the affected vessel. Using MPR, a slice image is reconstructed to show a longitudinal cross section of the vessel in the region of interest. An operator selects the orientation of the slice image to be reconstructed, whereby a portion of the longitudinal axis of the vessel is included in the image plane. The diameter of the vessel at a selected position in the selected image plane can then be measured by known methods.

It has been found that assessment of stenosis by measurements of vessel diameter is sensitive to a variety of operator-dependent factors. For example, an estimate of vessel diameter will depend critically on the selection of the image plane in which the diameter is measured. A misalignment of the tomographic slice (i.e., away from the vessel's longitudinal axis) may significantly affect the measured value of the diameter. The operator's skill and experience in selecting the best image plane for the multi-planar reconstruction therefore directly affects the accuracy of the assessment result.

The accuracy of the assessment also depends critically on the selection of the longitudinal position at which the vessel diameter is measured. Even an accurate diameter measurement will provide a reliable estimate of stenosis only when the measurement is taken at the position of greatest lumen narrowing. Hence, the selection of the longitudinal position at which to measure the vessel diameter also strongly affects the measured diameter value.

If the plane of the longitudinal cross section is selected carefully, then a trained technician or physician can visually identify the approximate longitudinal position of greatest narrowing. An image transverse to the vessel's longitudinal axis would be unsuitable for this purpose, because diameters along the longitudinal axis could not be compared. Consequently, it has been generally understood in the art that stenosis should be assessed from images oriented along the vessel's longitudinal axis. Indeed, U.S. Pat. No. 4,987,585, to Kidd et al., notes that stenosis may not even be apparent from images oriented transversely to the vessel's longitudinal axis.

Diameter measurements are also affected by the degree to which the vessel lumen diverges from roundness. If the lumen is oblong or irregular in cross section, then the lumen diameter will vary with the angular orientation of the selected image plane relative to the longitudinal axis of the vessel. The aforementioned patent to Kidd, et al., illustrates that this dependence of measured diameter on angular orientation of the plane of measurement is well known in the art. The conventional solution to this problem has been to generate several longitudinal cross sectional images of the constricted area at different angles.

The foregoing considerations also illustrate that quantitative assessment of structural features represented in tomographic images has been essentially a subjective process. Medical tomographic images and conventional radiographic images (whether generated by direct film exposure of by digital imaging methods) have been treated in much the same manner. In the typical procedure, an expert trained in medical image interpretation (a "reader") visually examines the image.

The aforementioned patent to Wilting shows that the reader may use computational aids to obtain measurements of vessel diameters. However, the foregoing observations illustrate some of the sources of assessment error that are associated with estimating the degree of stenosis based on lumen diameters. For example, if the lumen cross section is not round in the constricted area (a common situation), then a useful estimate of lumen size will still entail combining several diameter measurements from different images. The resulting quantitative assessment will depend on correctly selecting the particular images in which to make the measurements and the measurement locations in the selected images.

There has been recent interest in using volumetric data generated by other modalities to quantify vascular stenosis, such as magnetic resonance imaging (MRI). MRI uses magnetic polarization of imaged tissue and magnetic field excitation of the polarized atoms (e.g., by radio waves) to acquire volumetric data. As in CT, the volumetric data are then reconstructed to generate a three-dimensional (3D) model of the structure or organ of interest.

Using MR images, an organ's vasculature may be segmented from the surrounding tissues and the amount of stenosis determined, typically through visual examination of the generated images by a trained reader. MRI scans to produce medical images may entail many minutes to acquire volumetric data corresponding to the region of interest More generally, the greatest advantage of MR imaging for assessment of vascular stenosis has been the increased resolution and accuracy of the resulting images, relative to conventional angiographic techniques. These benefits have tended to increase the accuracy and repeatability of subjective assessment. Hence, the MR imaging modality has been considered as an approach by which the results of convention assessment methods could be improved.

CT imaging systems, MRI systems, and other imaging systems are or may be capable of rendering volumetric images from which segmentation of the vessel from adjoining tissue may be performed. However, frequently the reconstructed images will depict the structure of interest in an inconvenient orientation for purposes of examining particular structural features. The general result has been reduced precision for the assessment to be performed.

It follows that a tangible need continues to exist for a technique by which extensional features in images, such as diagnostic images, can be reliably and objectively quantified. Desirably, such quantification techniques could be readily implemented with the existing technology for tomographic imaging, as well as with other imaging modalities. Even more desirably, the quantitative assessment results thereby obtained would be relatively insensitive to confounding factors such as image noise, image artifacts, and operator selection of imaging parameters.

Ideally, such an approach could be applied to provide improved assessments of vascular stenosis, such as arterial stenosis, but could also be applied in a broad range of medical and non-medical application areas. The desired techniques would be readily applied in a range of areas where quantification of structural dimensions or other extensional features is needed and is currently unfeasible or subject to poorly constrained sources of error.

Here, the term "extensional feature" means a dimension, extent, characteristic, or property of an imaged subject that can be quantified by measuring a structural feature of the subject. An extensional feature typically will be a spatial extent of the structural feature, such as length, width, height, area, or volume. Alternatively, an extensional feature may be a non-spatial feature related to such a spatial extent of the structure by a known or determinable relationship.

A particular need exists for imaging and analysis methods and systems, such as x-ray CT systems with or without ancillary image processing systems, by which stenosis in vasculature structures can be reliably assessed. Such an approach would most desirably make evaluation of vascular stenosis a routine procedure. The substantial clinical benefits of such a technology would include, for example, significant reduction in variability of results due to differences of judgment between different readers. Further, because any necessary contrast medium could be injected into the peripheral vasculature, the desired technique would be only minimally invasive.

BRIEF SUMMARY OF THE INVENTION

The present invention satisfies the foregoing and other needs by providing an objective and repeatable approach to quantification of features from multidimensional image data. In a first aspect, the present invention provides methods, apparatus, software, and systems for image data analysis. A method of this first aspect may comprising fitting a profile from a selected family of profiles to a selected portion of image data representing an imaged object, and computing a magnitude of an extensional feature of the imaged object based on the fit profile.

A second aspect of the invention provides methods, apparatus, software, and systems for quantifying stenosis of a vessel from volumetric image data representing a three-dimensional portion of the vessel. A method of the second aspect may comprise obtaining a plurality of successive image data sets based on the volumetric image data, each image data set representing a transverse cross section of the vessel with respect to a central axis thereof at a corresponding successive axial position. A corresponding profile is selected for each image data set from a selected family of two-dimensional Gaussian profiles by fitting the corresponding profile to pixel data comprised in the image data set and representing a lumen of the vessel. Area values are determined for the lumen at the corresponding axial positions from the selected profiles. A further profile is selected from a selected family of one-dimensional profiles by fitting the further profile to the area values along the central axis. Stenosis of the vessel is quantified based on the further profile.

A third aspect of the invention provides methods, apparatus, software, and systems for structural assessment imaging. A method of the third aspect may comprise calculating quantitative information representing a structural feature of a volumetric structure in an imaged object, based on volumetric image data representing the imaged object. Sectional image data are generated specifying a cross sectional image of the volumetric structure in a plane selected based on the quantitative information. A profile from a selected family of profiles is fit to at least a portion of the sectional image data. A magnitude of an extensional feature of the volumetric structure is computed based on the fit profile.

A fourth aspect of the invention provides methods, apparatus, software, and systems for quantifying stenosis of a vessel from volumetric image data representing a three-dimensional portion of the vessel. A method of the fourth aspect may comprise obtaining a plurality of successive slice image data sets based on the volumetric image data, each slice image data set representing a transverse cross section of the vessel with respect to a central axis thereof at a corresponding successive axial position. A data portion comprising pixel data corresponding to a lumen region of the vessel is identified in each slice image data set. A sum of brightness values of the corresponding pixel data is generated for each slice image data set. Area estimates are determined for cross sections of the lumen region at the corresponding axial positions based on the sums. Stenosis of the vessel is quantified based on the determined area estimates.

As an aid for practicing the present invention, also disclosed herein are a method, an apparatus, and a computer-readable medium storing a program in which volumetric images are reformatted into one or more two-dimensional (2D) representations at selected plane orientations. The selected orientations of the reformatted 2D image planes can be chosen to provide desirable orientations of a feature or features depicted in the reformatted images. In a desirable embodiment, the invention provides an approach to reformatting volumetric images of blood vessels onto special 2D grids which facilitate assessment of stenosis.

BRIEF DESCRIPTION OF THE DRAWINGS

Further features and advantages of the present invention, as well as the structure and operation of various embodiments of the present invention, will become apparent and more readily appreciated from the following description of the preferred embodiments, taken in conjunction with the accompanying drawings of which.

DETAILED DESCRIPTION OF THE INVENTION

Figure 1:
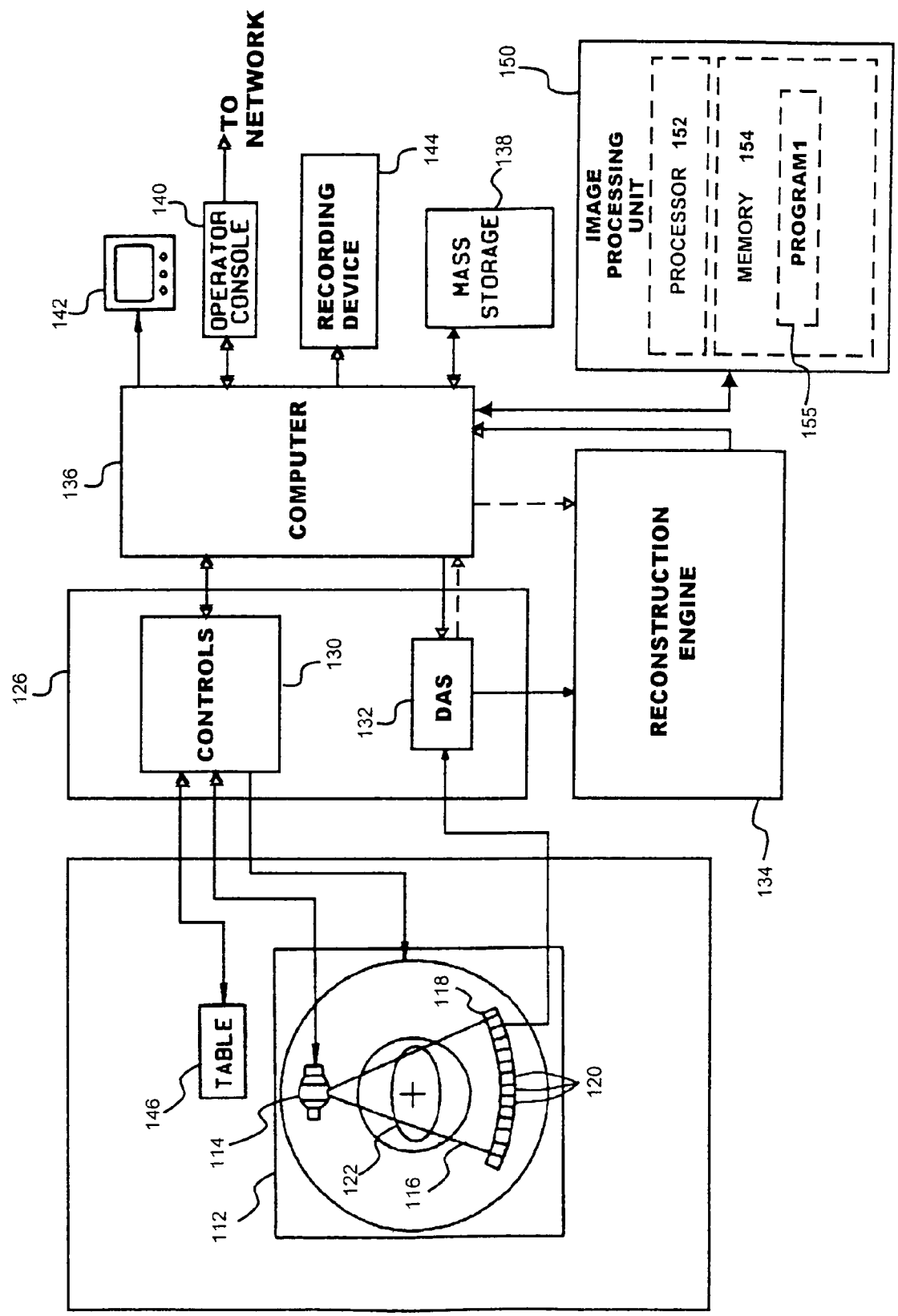
FIG. 1 is a schematic illustration of a CT imaging system.

Reference will now be made in detail to the presently preferred embodiments of the invention, examples of which are illustrated in the accompanying drawings, wherein like reference numerals refer to like elements throughout.

FIG. 1 is a schematic illustration showing the major components of a CT imaging system 100 in which the present invention may be incorporated. The CT system 100 desirably comprises a source-detector assembly 110. In some systems, such as so-called third generation scanners ("fan beam" systems) and some helical scanners, the assembly 110 may comprise a gantry 112. An X-ray source 114, such as a typical X-ray tube, produces a beam 116 of illuminating x-rays from which projection data may be obtained.

For purposes of clarity, the following description will specifically describe the fan beam case. Those of ordinary skill in the art will readily recognize and appreciate the occasional differences between third generation and fourth generation systems and between fan beam systems and cone beam/multiple-row helical scanning systems. The present invention may be readily applied to projection data obtained from all such x-ray tomography systems, from MRI systems, from ultrasound systems, and from other types of imaging systems capable of generating volumetric images.

Moreover, it is specifically noted that the imaging system of the present invention, when implemented in a CT imaging system, is not limited to a third-generation CT imaging system. The invention may be alternatively implemented in a so-called fourth-generation CT imaging system. In either the third-generation CT case or the fourth-generation CT case, the CT system may be either a fan-beam or cone-beam system operating in a mode to acquire the appropriate 3-dimensional data.

Throughout the following explanation, the terms "x-ray imaging system", "x-ray radiography imaging system", "computed tomography imaging system", and "CT imaging system" are used interchangeably to refer to the imaging system 100.

The source 114 may be mounted to the gantry 112 together with a detector array 118. Rotation of the gantry 112 thereby serves to rotate both the source 114 and the detector array 118 about a center of rotation 119. Alternatively, for example in so-called fourth generation systems, the detector array 118 is stationary with respect to the center of rotation 119, and only the source 114 rotates. In is mounted on the gantry 112 and rotates with rotation of the gantry 112.

Source 114, which may comprise a collimating element (not shown), projects the x-ray beam 116 toward the detector array 118 disposed opposite the source 114 relative to the gantry 112. The beam 116 may comprise a thin, fan shaped beam of radiation. Hence, "thin" here refers to the direction transverse to the fan plane.

The detector array 118 is typically comprised of numerous individual detector elements 120. An alternative term in the art for an array such as detector array 118 is "a multi-channel detector." It will be understood that either term is intended to mean a multiple-channel detection device usable in a computed tomography system.

Detector elements 120 together provide information regarding the internal structures of a subject 122. In the typical medical application of CT scanning, the subject 122 is a human patient undergoing medical evaluation or testing. Alternatively, in a veterinary context, the subject 122 may be an animal patient. In a still further alternative application, the subject 122 may be an inanimate object being subjected to, for example, nondestructive testing or examination. In any case, each detector element 120 generates an electrical signal indicating the intensity of a portion of the x-ray beam 116 impinging thereupon.

The particular system shown in FIG. 1 is indicated for purposes of illustration only. Thus, in the medical imaging context, the present invention also applies to tomographic image data generated by ultrasound or magnetic resonance imaging techniques. More generally, the present invention also applies to tomographic images generated in other application areas such as, for example, nondestructive testing and modeling of geological formations.

In the system 100 of FIG. 1, the signals from detector elements 120 indicate the attenuation of the beam 116 as the x-rays traverse the material of the imaging subject 122. Typically the source 114 is rotated around the imaging subject 122 during a scan operation to acquire x-ray data. Rotation of the source 114 may be implemented by rotation of the gantry 112 and the components mounted thereto (including the source 114).

The rotation operation for the source 114 is controlled by a control/interface system 126. A controls section 130 of the control/interface system 126 provides control for both positioning (such as gantry speed and position) and x-ray generation (power and timing) of the source 114. The control/interface system 126 also includes a data acquisition system (DAS) 132 that samples analog data from the detector elements 120 and converts the sampled data into digital data for further processing.

A reconstruction engine 134 receives the sampled and digitized data (now termed "projection data") from the DAS 132 and performs high-speed image reconstruction. Various algorithms are known in the art for reconstructing a slice image from projection data comprising a plurality of projection views. The reconstruction engine 134 sends the reconstructed image to, for example, a system management computer 136 for storage or display. Computer 136 may store the image in a storage 138, preferably as a data array.

The different functions of control/interface system 126, reconstruction engine 134, and computer 136 are desirably implemented on dedicated modular platforms, as described. However, the division of functions described herein is for purposes of example only. Such functions may alternatively be implemented in software, on a single computational platform, or in a different arrangement on multiple hardware platforms.

The computer 136 also receives commands and scanning parameters through an operator console 140. Output of the reconstructed image, as well as operational data and other information, may be performed through a video display 142 (such as a CRT display, flat panel display, etc.). The reconstructed image may optionally be directed to a recording device 144, such as a film recorder. Alternatively, the image may be transmitted as image data over a network (not shown) for disposition at another location.

Commands and parameters may be supplied through the console 140 to provide control signals and other information to the control/interface system 126. Further control of the imaging process is achieved by positioning the imaging subject 122 on a motorized table 146 under the control of signals from control/interface system 126. In a typical case, translation of the table 146 moves the imaging subject 122 relative to the source 114 and detector array 118 within a subject aperture 148.

FIG. 1 also shows an image processing unit 150 in which a particular embodiment of the present invention may be implemented. The image processing unit 150 may comprise a processor 152 (or perhaps several such processors) and a memory 154, which likewise may comprise several individual devices. In one aspect, the present invention provides an apparatus for processing projection data from tomographic imaging systems to generate quantitative estimates regarding the size of structural features represented in the data. Such an apparatus is embodied in FIG. 1 as the image processing unit 150. The image processing unit 150 carries out a method of the invention by executing an appropriate program 155, designated by reference numeral 155 in FIG. 1 and denoted PROGRAM1.

Alternatively, an apparatus of the invention may be embodied in the computer 136 by appropriate programming, or even in the reconstruction engine 134. Still another alternative embodiment of the invention comprises a separate image processing computer (not shown), which may be in communication with the system 100 of FIG. 1 through an appropriate data network or other data communication mechanism.

Figure 2:
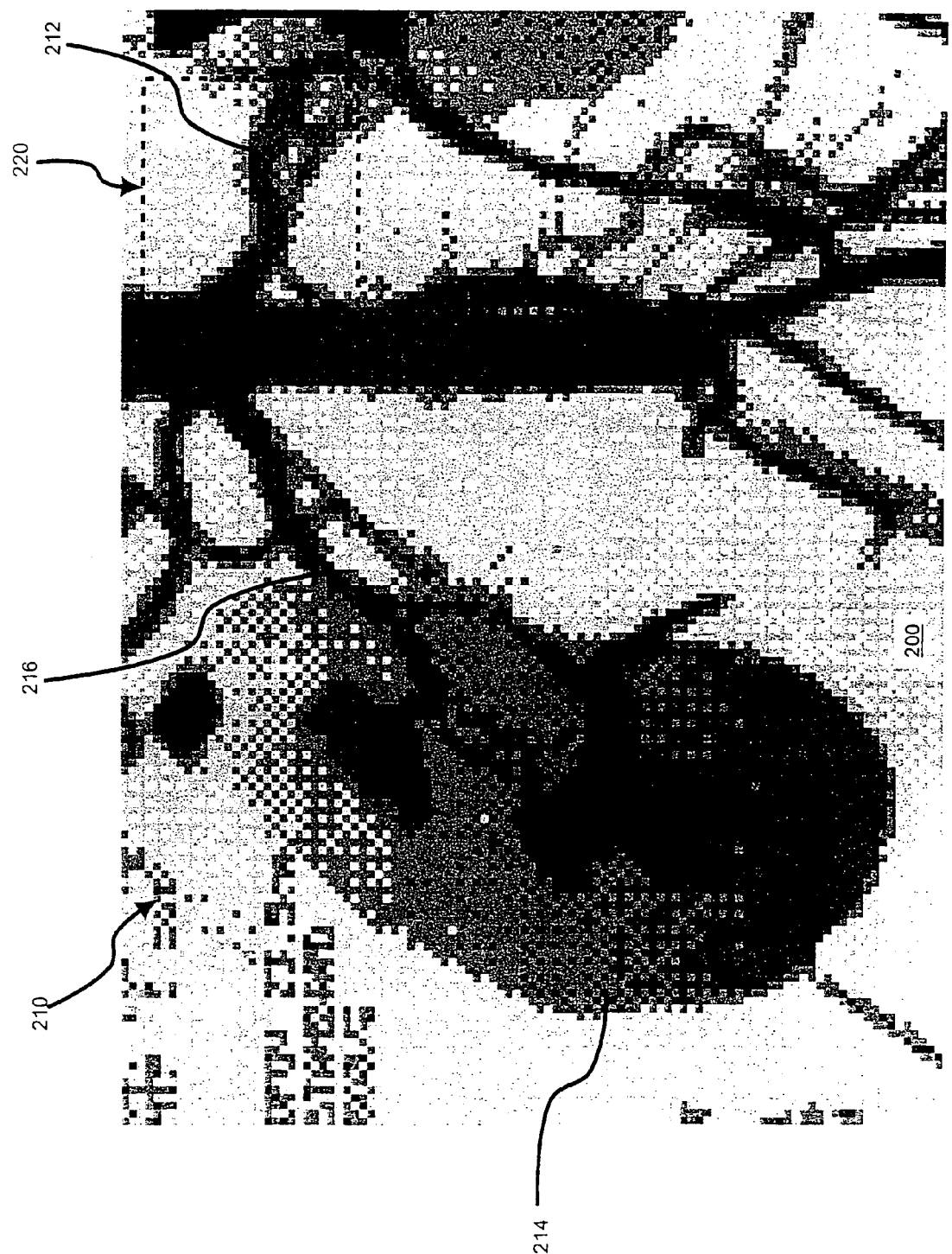
FIG. 2 illustrates a portion of an image such as a tomographic image.

FIG. 2 shows a portion of a typical tomographic image 200 generated by an imaging system such as system 100. This image portion is actually a portion of a tomographic image generated from projection data of a patient's abdomen. For convenience of illustration, the pixels of image 200 are shown with inverted pixel values. That is, in FIG. 2 darker shaded pixels correspond to greater brightness values. White or light gray pixels correspond to relatively smaller brightness values.

The image of FIG. 2 contains a primary structure 210, which happens to comprise the patient's kidneys and associated vasculature. The structure 210 includes various image features such as an artery 212, which in the present example is a renal artery. Here an "image feature" is a perceptible feature in the image, that is, a discernible, spatially localized pattern of pixels. A kidney 214 is shown in cross section. Also shown is a second renal artery 216 opposite the artery 212 and supplying the kidney 214. Readers trained in interpretation of medical images can easily identify the anatomical structures corresponding to image features in such a tomographic image.

More generally, a tomographic image may contain a variety of different image features representing different types of structures in the imaged subject. Here "imaged subject" is intended broadly to mean an entity or object of which the tomographic image represents at least a portion. Such an entity may comprise a portion of fluid or solid material, or several such portions, and may comprise rigid parts or elastic parts or both. In particular, although examples of the present invention will be described with reference to medical images, the invention broadly comprises techniques for feature quantification in numerous other application areas as well.

In the medical imaging context, the imaged subject is generally an animal (or possibly a plant) and most commonly is a human patient seeking medical evaluation or treatment. In nondestructive testing, the imaged subject is typically an inanimate object: a machine part, a casting of material (e.g., solid booster rocket propellant), etc. The imaged subject may even be a portion of material integrally comprised in a larger body, such as a portion of a subterranean formation of rock or sediment.

A tomographic image may depict a cross-sectional view of the imaged subject at a particular axial position, such as the slice image 200 of FIG. 2. Alternatively, a tomographic image may be a three-dimensional image generated from volumetric projection data or from tomographic image data for several slice images at a succession of axial positions (so-called "stacked 2-D slices"). Other techniques for generating a cognizable view of the imaged subject from tomographic image data may also be possible and are within the intended meaning of "tomographic image."

A typical tomographic image, such as image 200 in FIG. 2, is composed of an array of picture elements, or "pixels." The pixel array is a two-dimensional or three-dimensional array of points corresponding to a two-dimensional or three-dimensional array of data elements. The data elements (or "pixel data") of the data array respectively specify image information for the pixels of the resulting image and collectively define the image.

Typically the data element for a pixel comprises information identifying the pixel's relative position in the image and a particular numerical value associated with the pixel position and denoted here as a "brightness value." The brightness values of the pixels will typically represent the visual brightnesses of the pixels in the image according to a specified brightness scale, such as a 256-level gray scale. However, it may be possible for the brightness values of an image data array to represent, for example, color levels according to a specified color scale. Persons of skill in the art will readily appreciate that other scale-associated level information may be represented by the brightness values of the image pixels.

The image is a visual representation and thus provides perceptual information about the imaged subject. In particular, an image feature typically represents a corresponding structural feature of the imaged subject. The image feature thereby conveys some information about the structural feature. For example, in FIG. 2 a detail 220 comprises part of the renal artery 212. The size of the actual vessel may be perceived from the width of the artery 212 considered as part of the image 200.

In theory, the width of the artery 212 could be determined by measuring the width of the structure 212 directly, when the image 200 is displayed or printed. As may be seen from the image 200 of FIG. 2, however, the various image features in a reconstructed or radiographic image are typically somewhat indistinct, i.e., blurry or fuzzy. Such an image feature therefore usually lacks a precise boundary with which to define the spatial extent of the image feature. Direct measurements from the rendered image therefore entail an element of judgment in determining points between which to measure.

The aforementioned patent to Wilting offers a method for addressing this problem in the specific context of measuring a width of a bright image feature, such as the lumen of a longitudinally sliced vessel. A region clearly inside the feature is identified, and regions clearly outside the feature are also identified. Because the feature is assumed to be brighter than the surrounding regions, the pixel brightness values will tend to follow a gradient between the bright region and the darker regions. The method accordingly selects from either side of the bright region pixels having brightness values a specified fraction of the maximum brightness value within the feature region. An arithmetic processor can automatically calculate the distance between the selected pixels, based on their respective positions.

The diameter measurements do not directly represent the cross sectional area of the subject vessel. Therefore, the technique of Wilting does not extend to direct measurement of higher-dimensional quantities, such as areas and volumes. Nevertheless, by comparing diameters inside and outside the constricted region, the degree of stenosis (expressed as a percentage) can be assessed.

The present inventors have observed that, other things being equal, an estimate of stenosis by ratio of diameters will tend to be particularly sensitive to measurement errors. This is because area scales as the square of diameter. For example, with a 50% stenosis (50% area reduction), the reduced area $A_2$ is one-half the original area $A_1$: $A_2=A_1/2=0.50A_1$. But the reduced diameter, $d_2=[4A_2/\pi]^{1/2}$, is less than the original diameter $d_1$ by a factor of $1/\sqrt{2}$: $d_2=(1/\sqrt{2})d_1 \cong 0.707d_1$. This means that an error in the measurement of the reduced diameter causes an exaggerated error in the estimated area reduction. Thus, assessment of stenosis by diameter measurements is intrinsically sensitive to measurement errors.

More fundamentally, in the approach of Wilting the measured value (e.g., diameter) is determined by only a few distinctive pixels inside and outside the image feature of interest. This limitation imposes an implicit assumption that the pixels forming the image feature will have brightness values that vary from pixel to pixel in a known manner. But in real tomographic images, such an assumption may not be valid.

Figure 3:
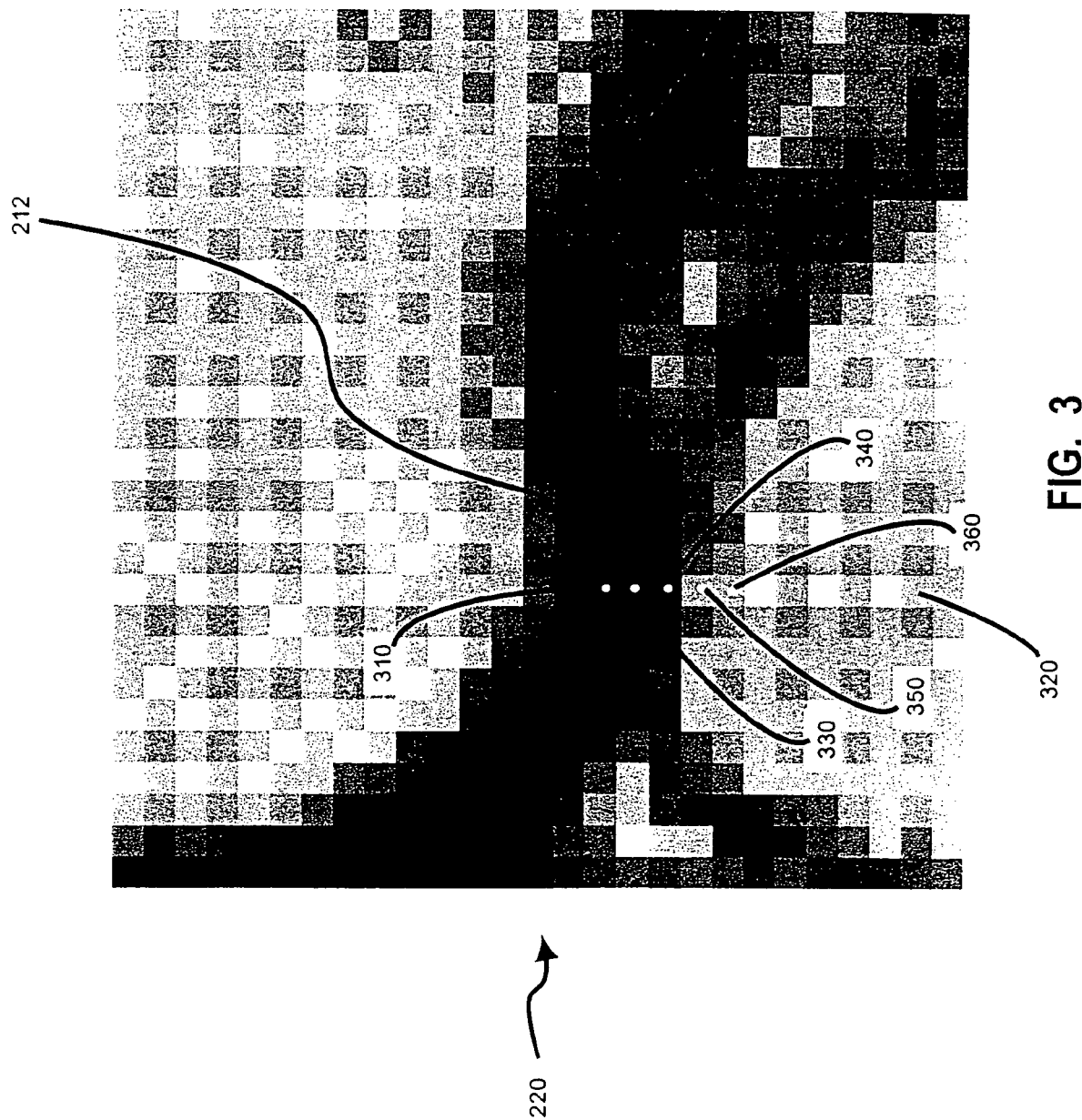
FIG. 3 illustrates a detail from the image portion illustrated in FIG. 2.

FIG. 3 illustrates the detail 220 from FIG. 2 in magnified form. (Again, as in FIG. 2, the pixels of FIG. 3 are depicted with inverted brightness values.) It is apparent that the pixel brightness values of the artery 212 do not vary in a regular manner. For example, the pixel 310 within the artery 212 is relatively dark (high brightness), and the pixel 320 outside the portion 212 is white or light gray (corresponding to a low brightness value). To estimate the width of the portion 212 from these two brightness values, the contour of brightnesses should at least strictly increase between the pixel 310 and the pixel 320.

As FIG. 3 shows, though, two equally bright pixels 330 and 340 occur between pixels 310 and 320. Moreover, even if pixels 330 and 340 are considered too bright (too dense) to indicate the boundary of the artery 212, the next pixels 350 and 360 are also of equal brightness. In such a situation, it will be difficult to determine a unique pixel having a brightness value equal to a predetermined fraction of the maximum (or minimum) brightness value.

A General System for Feature Quantification

Figure 4:
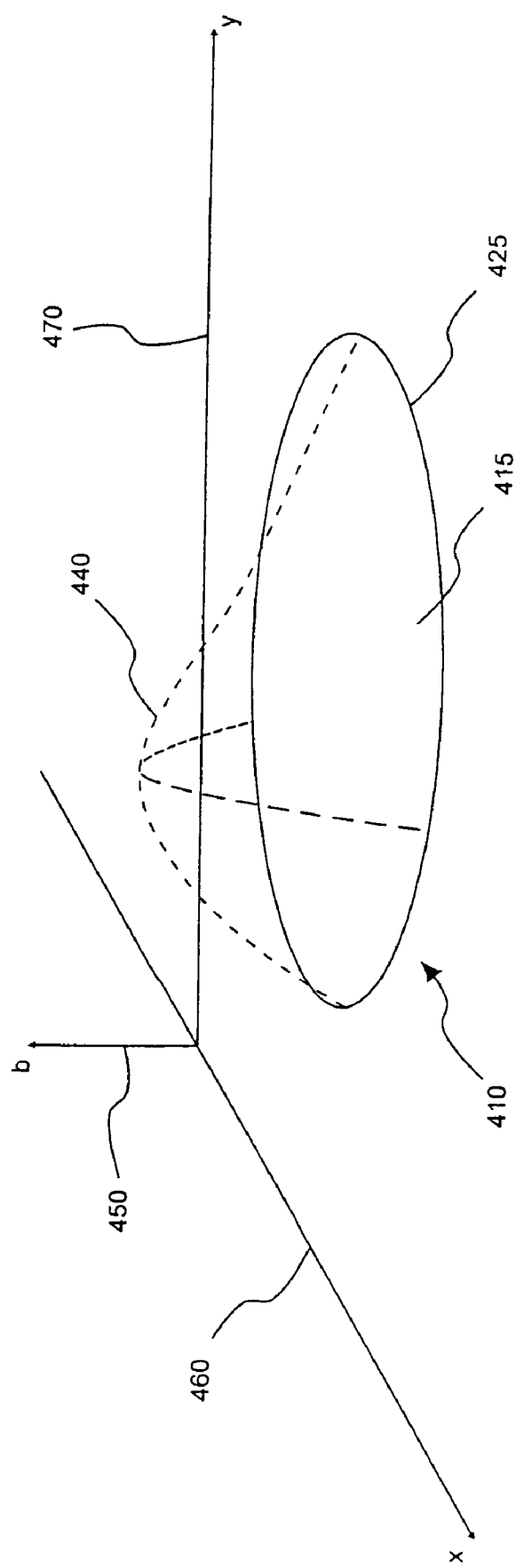
FIG. 4 is a schematic diagram of an image feature from an image such as a tomographic image.

FIG. 4 is a schematic diagram of an image feature 410 from such a tomographic image. The image feature 410 is a portion of a digital image representing a structure of an imaged subject. The example illustrates the case where the feature 410 is a portion of a two-dimensional image and extends in two directions (x and y). However, the above discussion makes clear that such a image feature may alternatively extend in one or three dimensions. If the image were a three-dimensional view of the structure, then such a feature could possibly extend in three directions.

An image feature such as feature 410 may be enclosed within a well-defined boundary in the image, or alternatively may comprise an open region. In the illustrated example, the image feature 410 comprises an interior region 415 separated from the surrounding regions of the image by a boundary 425. In the two dimensional case illustrated, the region 415 occupies a particular area of a two-dimensional tomographic image. In the case of a three-dimensional image, such an interior region may occupy a particular volume of the 3D view.

In a typical case, an image feature in an image may be identified by a difference in overall brightness between the region of the feature and surrounding regions. In FIG. 2, for example, the artery portion 212 appears in the image 200 as denser (corresponding to greater pixel brightness) than the adjacent material above. Similarly, the vessel 216 is denser than the kidney portion 214 and other material adjoining the vessel 216. It is well known that image regions with contrasting brightness levels generally represent different structural components of the imaged object.

The contour 440 is shown as extending in the positive b direction, relative to the surrounding regions. This orientation reflects the exemplary case where the image feature 410 appears brighter than the surrounding features of the image. If the feature 410 were darker than the surrounding regions (like the vessel portion 212 in FIG. 2, for example), then the contour of pixel brightnesses would extend in the negative b direction, relative to the surrounding regions. Moreover, an image feature in a three-dimensional image will have pixel brightnesses that define a stepwise constant function of three independent variables x, y, and z.

For purposes of specificity in the illustrated example, it is assumed that the feature 410 is distinguished from surrounding regions by being relatively brighter. The brightness levels of the pixels accordingly form an upwardly convex contour such as the contour 440, shown in outline in FIG. 4. The case where an image feature is darker than surrounding regions is similar, but the contour defined by the pixel brightness values is upwardly concave.

In other words, the contour 440 is defined by brightness values relative to a b-axis 450. The pixels of the feature 410 consequently have brightness values defined by a function of two dimensions x and y measured along axes 460 and 470, respectively. The brightness function takes values (brightness values) measured along the b-axis 450. It follows that the elevation of the contour 440 at the pixel position (x,y) represents the brightness of that pixel. Moreover, the pixel positions (x,y) are discrete points in the image region, and each pixel has a single brightness value. The brightness of an image is thus said to be "discretized" by the discrete pixels, both in spatial distribution (discrete pixel positions) and in brightness level (e.g., brightness levels selected from 256 discrete brightness values). Hence the brightness function defined by the pixel brightnesses (graphed as the contour 440 in FIG. 4) will generally be a discontinuous, piecewise constant function.

The size or other extensional features of a structure shown in a tomographic image may provide important information regarding handling or treatment of the imaged subject. For example, if the structure is a blood vessel, then the cross-sectional area of the vessel lumen can indicate whether the patient has vascular stenosis requiring therapy. A bubble in the material of a casting or a machine part may, if sufficiently large, cause a hidden structural weakness in the part or casting. Thus, the present invention is directed generally toward providing the ability to measure or estimate an extensional feature of a structure (such as the size of the lumen of a blood vessel) from an image feature representing the structure. The capability provided by the invention is desirable in medical assessment and diagnosis, as well as in many other areas of application.

The present invention proceeds from the recognition that the inherent blurriness of tomographic images makes direct measurement of image features difficult and uncertain. Trained readers are able to make quantitative assessments from tomographic images, at least in some circumstances. However, as noted above, the need for skilled personnel to generate and interpret the images raises important issues relating to reliability and repeatability of such assessments.

Heretofore a central objective of medical imaging has been to provide accurate images for examination and evaluation by technicians and physicians. The problem to be solved has been to produce a visually intelligible image from large quantities of data representing individual detector responses. The goal has thus been to generate from quantitative data the best possible images for visual examination and assessment. The underlying rationale, like more typical applications of data visualization, has been that the underlying data are too numerous and complicated to be amenable to direct quantitative analysis. Accordingly, it has been understood in the art that the data should be converted into an image that can be evaluated by visual perception.

The present invention proceeds in a direction different from the accepted understanding in the art regarding effective interpretation of tomographic images. In one aspect, the present invention implements the discovery that computational analysis of the image data can produce quantitative assessments that are more reliable than visual estimation and known measurement techniques. On one hand, the invention makes use of information contained in the spatial relationships between the pixels that make up an image feature.

The quantitative results of the present invention are therefore more reliable than conventional measurements based on a few isolated pixel values. The invention thus exploits the fact that the image data represent an image feature having specific geometrical characteristics. On the other hand, direct quantitative analysis of the image data itself is contrary to the understood purpose for which such image data are conventionally generated, i.e., for visual assessment from the resulting image.

An aspect of the present invention is the discovery that quantitative analysis of the brightness contour for a given image feature can provide useful information about the imaged object. The invention employs the observation that fitting a profile to the pixel brightness data can produce information that quantifies a specific extensional feature of the imaged object. Fitting a profile to the pixel data of an image feature will generally produce one or more parameter values. In particular, the profile may be selected (i.e., "fit") from an appropriate family of profiles according to an appropriate selection criterion. The one or more parameter values may then provide an accurate and repeatable estimate of an extensional feature (length, thickness, area, volume, etc.) of the structural feature represented in the image.

Here a "profile" is function defined by a set of one or more analytical expressions on a corresponding domain. A profile may be used to approximate a contour defined by a set of data values associated with corresponding points in the domain. Typically an analytical expression is defined precisely by one or more mathematical formulas containing a number of coefficients. A particular set of values for the coefficients will precisely specify the formula (or formulas) and hence will completely define the profile.

For example, the polynomial expression $p(x) \equiv a_0 + a_1 x + a_2 x^2$ contains coefficient parameters $a_0$, $a_1$, and $a_2$. The expression $$g(x) \equiv p(x) + a_3 e^{-\frac{1}{2}\left[\frac{x-a_4}{a_5}\right]^2} \quad (1)$$

contains the parameters $a_0$, $a_1$, $a_2$, $a_3$, $a_4$, and $a_5$. These expressions will define particular profiles, if the parameters are assigned specific values. The particular values may be chosen by, for example, linear regression (i.e., least squares fit).

A profile may be a function of one or more independent variables. For example, the image feature 410 shown in FIG. 4 extends in two dimensions (x and y), and the brightness contour 440 extends in a third dimension (b). A profile to approximate the contour 440 will typically be a function of the two independent variables x and y and will define values for the dependent variable b. A profile fit to an image feature in a three-dimensional tomographic image will typically be a function of three independent variables. Of course, if the image feature has lower dimensionality than the image, then the profile may be defined parametrically with fewer independent variables.

It is also possible to define a profile as a combination of piecewise-defined functions, such as by a spline interpolation method or a collocation method. A further alternative is to define the profile as a combination (i.e., a superposition) of independent basis functions, such as by a finite element method or a wavelet method. Further alternatives will be apparent to those of skill in the arts of numerical analysis and computational modeling.

A "family" of profiles is a set of profiles specified by a common set of defining expressions in which the coefficients are represented as parameters. A particular profile in the family may be selected specifying particular values for the coefficient parameters. The one or more expressions with unspecified parameters therefore serve as a template function that may be selected in advance. An appropriate fitting operation determines specific values for the parameters, whereby a specific profile is selected (fit to the data) from the given family of profiles.

"Curve fitting" is sometimes defined as a computational procedure for determining, for a given type of curve, a particular curve that most closely approaches a specified set of points. Here an operation of "profile fitting" is a generalization of curve fitting procedures, for the particular case of determining profiles for sets of pixel data. It will be apparent to those skilled in the art that the pixel data may define points in several dimensions, such as in three dimensions (for a two-dimensional image) or in four dimensions (for a three-dimensional image).

A profile is "fit" to a set of pixel data by performing a computational procedure on the pixel data to determine, for a given "type" or "family" of profiles, a particular profile whose values match the brightness values of the pixel data at the corresponding pixel positions. In the simplest case, profile fitting may comprise determining a profile whose values coincide with the pixel data brightness values at the corresponding positions. In this case the profile that "most closely approaches" the pixel data is the profile with values that coincide with the pixel brightness values at the corresponding pixel positions. This type of profile fitting will be called "coincidence fitting," and the profile thereby obtained will be called a "coincident fit" profile. The numerous different methods for polynomial interpolation, for example, are instances of coincidence fitting methods.

A desirable alternative is to match the pixel data by determining a "best-fit" profile, in which case "most closely approaches" means that some abstract measure of separation is minimized. Here a best-fit profile is a profile for which a corresponding objective function evaluates to an optimal value (e.g., a maximum value or a minimum value) with respect to the given pixel data. The measure of separation thus corresponds to the value of the objective function, for the given set of pixel data and the profile under consideration.

For example, a profile may be fit to the pixel data by linear regression. In this case, the objective function is defined by the well-known quadratic form whose values are the sums of the squares of the differences between the profile values and the pixel brightness values at the corresponding pixel positions. The profile that gives the smallest value of this form for the given set of pixel data will be called here the best-fit profile "by least squares." Regression methods (such as for linear or non-linear regression) are well known in the art of statistical data analysis and will not be described in detail here. Moreover, those of skill in modern data analysis techniques will appreciate that other alternative procedures for fitting a function to a given set of data may be applied for profile fitting in the present invention.

According to the image feature of interest and the measurement to be obtained, the profile is fit to the data (i.e., selected) by carrying out an appropriate profile fitting operation. Here "measurement" means a determination (such as an estimate) of a magnitude of an extensional feature. A desirable criterion for appropriateness of the fitting operation is whether the comparability of the measurements is enhanced.

A difference between two measurements of similar extensional features may arise either from differences in the extensional features or from differences in the methods by which the measurements were obtained. If similar methods of measurement are used, however, the difference between the measurements can be attributed to differences in the underlying extensional features. It is therefore desirable to use a standardized fitting procedure for similar measurements.

It will also be appreciated that a measurement obtained from the selected profile may depend on the family of profiles. The comparability of the resulting measurements will tend to be enhanced by using a common family of profiles for similar measurements. Moreover, the accuracy of the measurements will also tend to be affected by the selected family of profiles. For example, a poorly selected family of profiles may introduce unacceptable systematic errors in the measurements. Another possibility is that the selected family may be relatively insensitive to the quantitative information to be extracted from the pixel brightness contour. It is therefore desirable to select the family of profiles according to the desired measurement and the type of image feature to be measured.

A contrasting procedure is commonly employed in statistical data analysis. The typical approach in such cases is to analyze sample data $(x_1, x_2, x_3, \ldots, x_n)$ with the goal of estimating a probability density $\phi(x)$ for the population. Typically it is assumed that the density distribution $\phi(x)$ generally conforms to a theoretical distribution $\phi(x)=\phi(x; \alpha_1, \alpha_2, \alpha_3, \alpha_4, \ldots, \alpha_n)$. Here the terms $\alpha_1, \alpha_2, \alpha_3, \alpha_4, \ldots, \alpha_n$ are so-called "population parameters."

In statistical analysis the sample data $(x_1, x_2, x_3, \ldots, x_n)$ are used to estimate values of these parameters. Usually the parameter value estimates provide information about the distribution of values that can be expected for the population represented by the random variable x, such as population mean, population variance, and so forth. The overall goal is to decide a present course of action most likely to succeed, based on estimated relative likelihoods of future events.

The present invention may employ some related computations, but the data analyzed and the results obtained are radically different. Instead of representing instances of a system subject to random variation, the image data processed in the present invention represent parts of a single view of a system (the imaged object). Together the image data represent geometrical information regarding a single instance of the object. Further, instead of providing estimates about the likelihood of other instances, the results of profile fitting in the present invention provide estimates about structural features of the single instance represented in the image.

These fundamental differences illustrate the radical departure made by the present invention, relative to model fitting in statistical analysis. Indeed, users of statistical methods are commonly warned about the consequences of applying such methods incautiously: "[i]ncorrect use of statistical methods can lead to grave errors and seriously wrong conclusions." See G. A. KORN, ET AL., MANUAL OF MATHEMATICS 197 (1967). A useful aspect of the present invention is the discovery that some of the same theoretical distribution functions used in statistical data analysis are also useful for modeling the representations of physical structures in tomographic images. The use of such functions for structural modeling purposes may be "incorrect" in the sense of statistical analysis, but the present inventors have discovered that such use can produce desirable results.

An advantage of the present invention is that useful quantitative information can be determined from the geometrical characteristics of the image feature in gross. Instead of relying on the positions and values of individual pixels, the invention also takes into account the spatial arrangement of the image feature, as represented in the pixel data. It has been found that the invention provides quantitative measurements that are relatively insensitive to image-specific factors such as noise, image artifacts, and operator-selected image analysis parameters.

Figure 5:
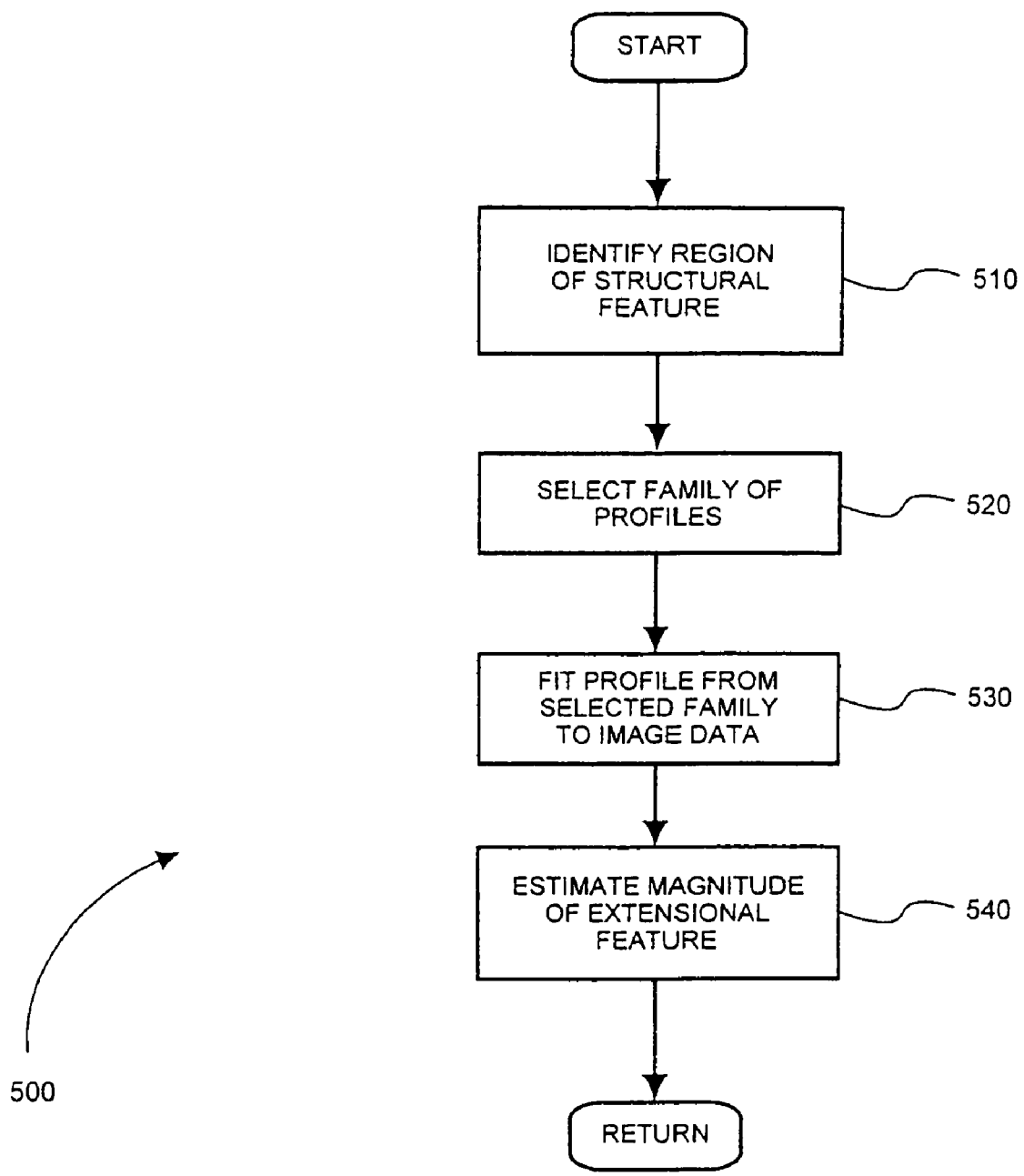
FIG. 5 is a flow diagram illustrating a procedure for an embodiment of the present invention.

FIG. 5 is a flow diagram illustrating a procedure 500 of the present invention. As FIG. 2 illustrates, a typical tomographic image will contain various image features. It is therefore desirable to specify the image data representing the particular feature of interest. Accordingly, the procedure of FIG. 5 comprises an operation 510 in which a region of the tomographic image is identified for further analysis.

The operation 510 may be performed by a human operator, or possibly with appropriately configured pattern recognition software. However, even operator identification does not inject a significant source of subjectivity into the quantification procedure. It has been found that the fitting operation of the invention actually renders the estimates relatively insensitive to differences in the identified region.

In an operation 520, an appropriate family of profiles is selected for the measurement to be taken from the image feature. This operation may be performed before, concurrently with, or after the operation 510. If the image feature is identified by pattern recognition software, then the family of profiles may be selected based on the pattern recognition result. Alternatively, the procedure of FIG. 5 may be configured to estimate magnitudes for a specific class of extensional features, such as the cross sectional areas of vessel lumina. The selection of operation 520 may then be performed in advance to accommodate various selection criteria, such as insensitivity to image noise, absolute accuracy of the resulting measurements, computational efficiency, and so forth, or some combination thereof.

An operation 530 is then performed to fit a profile from the selected family of profiles to the image data of the identified image region. Based on the selected profile, such as by the parameter values therein, an operation 540 is performed to estimate the magnitude of the extensional feature of interest. A specific embodiment of the invention, and incorporating the procedure of FIG. 5, will now be described with reference to FIGS. 6-11.

Figure 6:
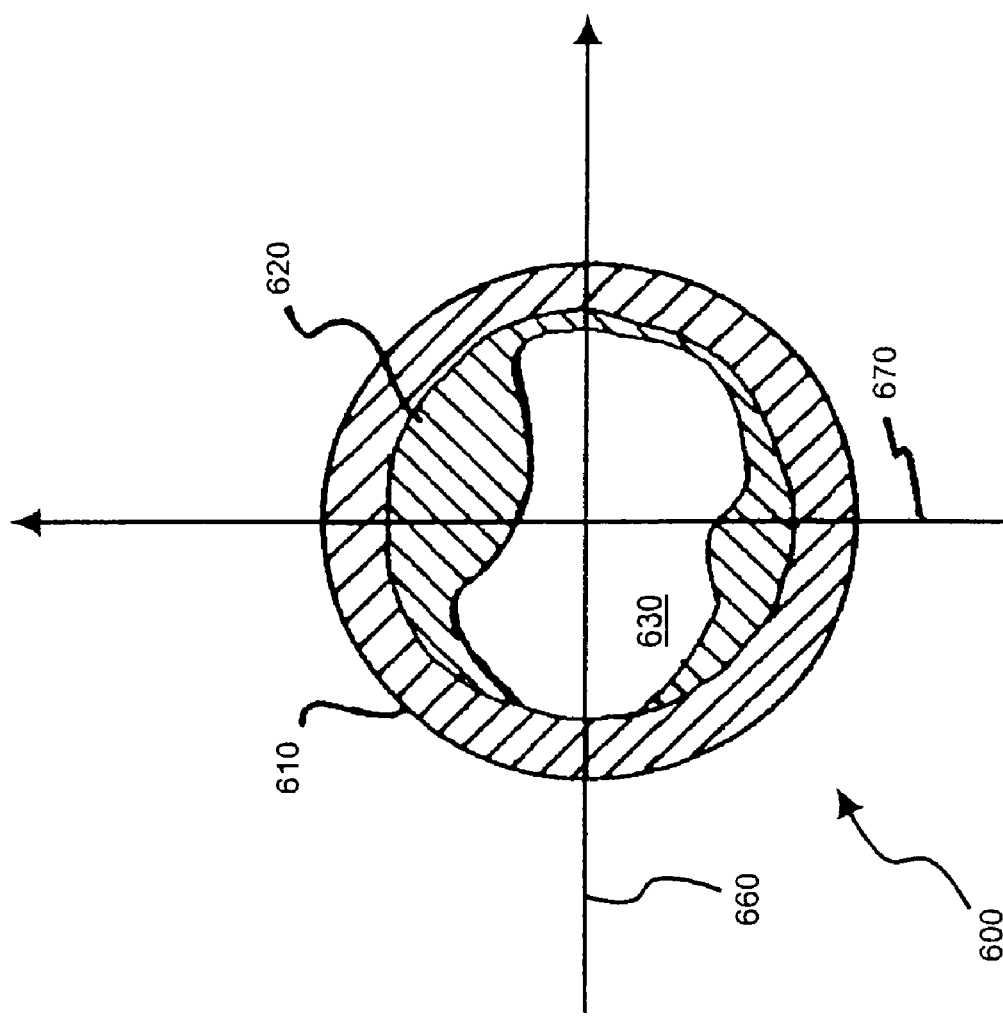
FIG. 6 is a schematic cross sectional view illustrating a partially blocked vessel.

FIG. 6 illustrates a transverse cross section 600 of a partially blocked artery 610. The interior of the artery 610 is partially blocked, at the location of the cross section, by an accumulation of atherosclerotic plaque 620. The residual lumen 630 is substantially reduced from the original size of the artery. The plaque 620 thus reduces the volume rate of blood flow through the artery 610 and can be a cause of serious symptoms and conditions. Such symptoms and conditions may include acute ischemia leading to pain, arterial occlusion, and ultimately may result in tissue death (infarction).

In the particular example of FIG. 6, the residual lumen 630 is roughly oblong in shape at the position of the cross section 600. The apparent size and shape of the lumen will typically depend on the axial position of the cross section 600. The orientation of the plane of the cross section (defined by the axes 660 and 670) will also affect the apparent features of the lumen. That is, the apparent lumen size and shape will usually depend on whether the plane is oriented obliquely to the longitudinal axis of the vessel or is perpendicular to the axis. In view of such variability, the accepted teaching in the art has been that quantitative assessment of stenosis cannot be performed reliably from such cross sectional views.

A tomographic image can be generated to depict an artery cross section such as the transverse cross section 600 of FIG. 6. However, as explained above, image features corresponding to the lumen 630 and the plaque 620 will be separated in the image by an indistinct boundary. Thus, even measuring the apparent size of the residual lumen 630 is a difficult and uncertain task by conventional methods.

Figure 7:
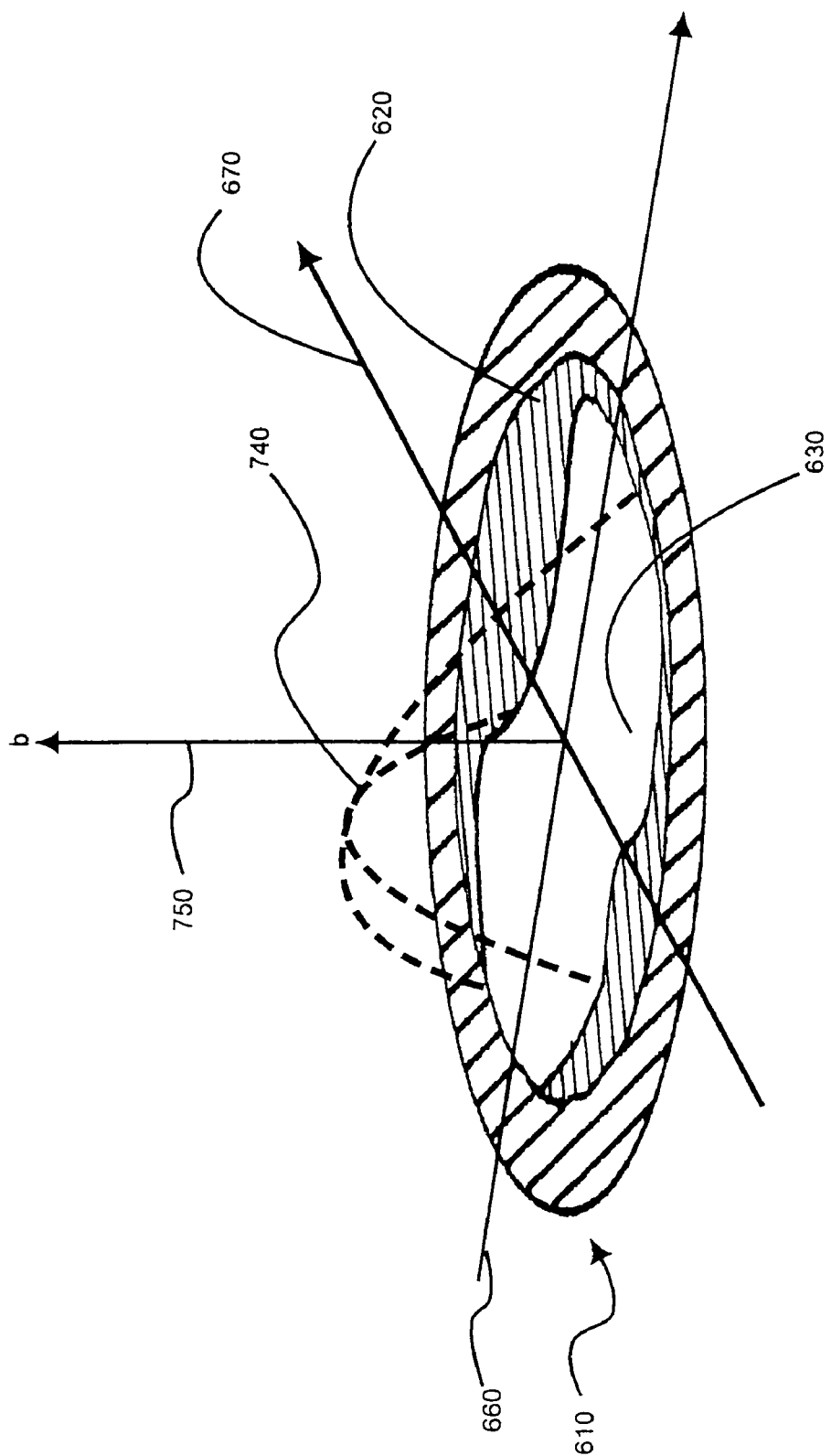
FIG. 7 is a perspective view of the vessel cross section shown in FIG. 6.

FIG. 7 is a perspective view of the vessel cross section 600 shown in FIG. 6. As discussed above, a tomographic image including a representation of the cross section 610 will be composed of an array of pixels having respective brightness values. The portion of the pixel data representing the lumen 630 will have brightness values defining a brightness contour 740. Like the contour 440 in FIG. 4, the contour 740 extends in a third dimension defined by a b-axis 750.

The level of the contour 740 on the b-axis 750 indicates the brightness value of the pixel at the corresponding position in the plane defined by the axes 660 and 670. Because the material composition of the vessel 610 and the plaque 620 differs from the composition of the blood in the lumen 630, the image will typically represent the lumen 630 as a relatively brighter region.

An aspect of the present invention provides an approach for estimating an extensional feature such as the area of the lumen 630 in the cross section 600. A reliable measurement of such extensional features will be useful in a variety of application areas for tomographic imaging. However, as noted above, the accepted teaching in the art has been that cross sectional images have serious disadvantages for assessing vascular stenosis. The present invention therefore provides, in a further aspect, an approach for assessing stenosis by combining plural area measurements along the longitudinal axis of the artery.

Methods embodying the various aspects of the present invention may be implemented in software to execute on a dedicated image processing platform such as the image processing unit 150 shown in FIG. 1. Alternatively, software to implement the invention may be designed to execute on another special-purpose platform such as the reconstruction engine 134 in FIG. 1. In a further alternative, such software may be configured to execute on a multiple-purpose computer such as the computer 136 of FIG. 1. The software may be configured for execution on a single processor or on a parallel processor arrangement, such as a dedicated multi-processor platform or a group of networked computers running a suitable parallel processing utility such as PVM.

A software program embodying an aspect of the invention may be encoded on a computer readable storage device such as a removable disk unit for the mass storage unit 138.

Figure 8:
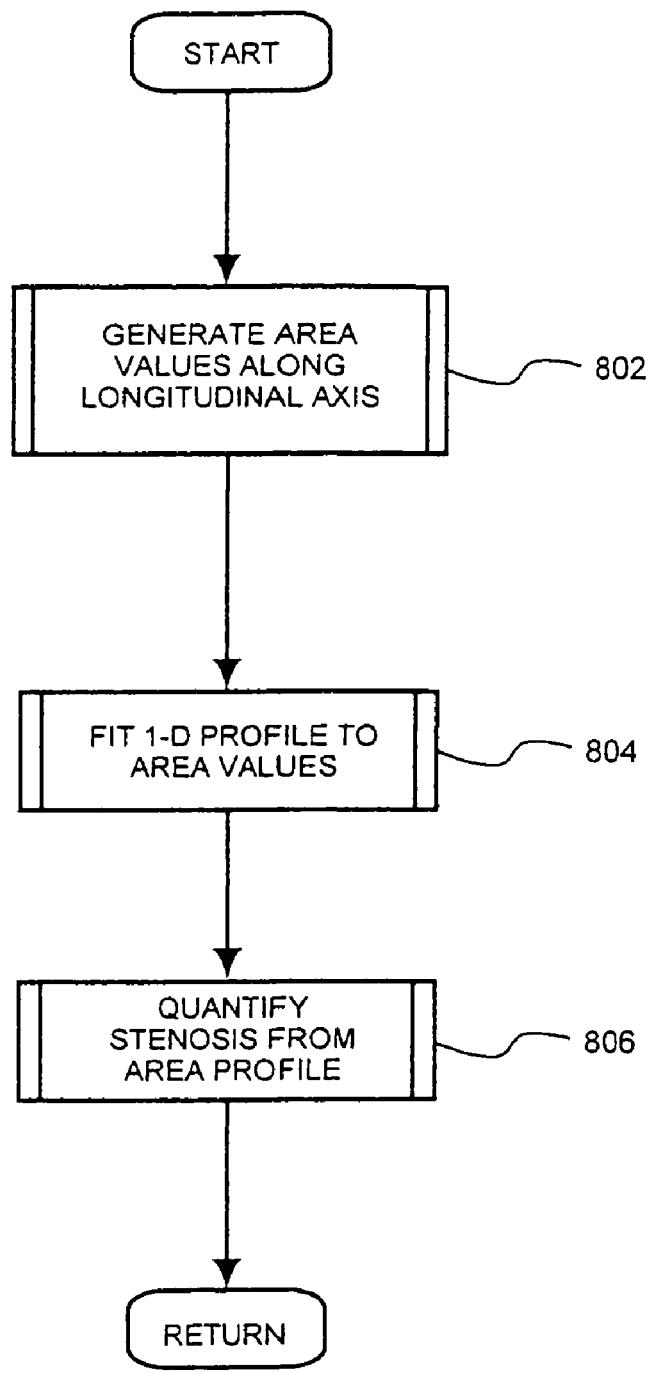
FIG. 8 is flow diagram illustrating major operations of a procedure of the invention.

FIG. 8 is a flow diagram illustrating an overview of a process embodying this further aspect of the invention. Lumen area estimates are generated at successive positions along the longitudinal axis in an operation 802. Such estimates may be obtained by the foregoing aspect of the invention, in which profiles are fit to the pixel data at the successive cross sections. Alternatively, the area may be estimated by summing the pixel values of the lumen area. In either case, one-dimensional profile is then fit to the obtained area estimates in an operation 804. Parameter values from the one-dimensional profile are processed in an operation 806 to obtain a quantitative assessment of stenosis in the imaged region of the vessel. These operations will be described in more detail with reference to FIGS. 9-11.

Figure 9:
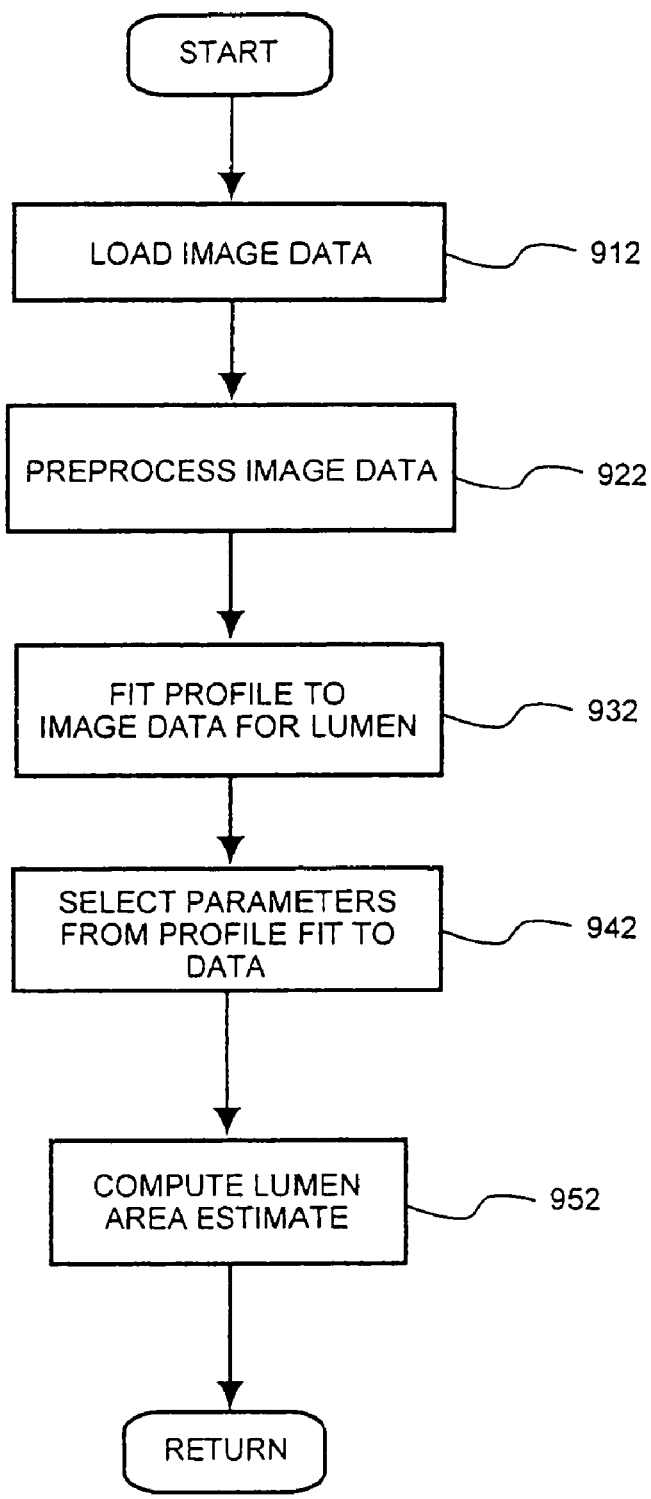
FIG. 9 is a flow diagram illustrating exemplary details of an operation of the procedure illustrated in FIG. 8.

FIG. 9 is a flow diagram illustrating exemplary details of an embodiment of the operation 802 of FIG. 8. Image data for a suitable tomographic image are loaded onto a selected processing system in an operation 912. In the particular case of assessing vascular stenosis, it is desirable for the image to represent an orthogonal cross section of the vessel at a selected axial position. The cross section will then depict the vessel in a plane perpendicular to the longitudinal axis of the lumen. To facilitate quantification in a case such as this, the image data may be preprocessed in an operation 922 to improve the results of the subsequent profile fitting and estimation operations.

A specific embodiment of a preprocessing procedure that may be included in the operation 922 will be described in detail below with reference to FIGS. 12-23. However, the present invention for feature quantification does not require such a procedure, nor does the invention require preprocessing at all. Indeed, some embodiments of the invention would realize little or no benefit from such preprocessing.

Desirable other preprocessing actions, if employed, may also depend on the characteristics of the profile fitting operation. For example, it may be desirable to enhance the brightness contrast between the lumen region and the surrounding regions. One technique for such enhancement is to scale the subrange of pixel values in the lumen region to fill the entire range of brightness values (e.g., 0 through 255). The image region to be fit may be enlarged by embedding the region of the lumen in a larger area of pixels with pixel brightness values equal to the minimum brightness value in the lumen region. This latter action may be desirable to ensure convergence of the fitting operation.

An operation 932 implements the profile fitting operation. The procedure is similar to the operations of FIG. 5, but here it is assumed that the fitting operation has been configured specifically for lumen area estimation. The following expressions define a family of profiles that have been used successfully to estimate vessel lumen areas:

$$z = F(x,y) = a_0 + a_1 e^{-u/2}, \tag{2}$$

where $$u = \left[\frac{x'}{a_2}\right]^2 + \left[\frac{y'}{a_3}\right]^2, \tag{3}$$

$$x' = (x-a_4)\cos a_6 - (y-a_5)\sin a_6, \text{ and} \tag{4}$$

$$y' = (x-a_4)\sin a_6 - (y-a_5)\cos a_6. \tag{5}$$

The expression (2) defines a standardized form of a so-called "Gaussian profile." Here a Gaussian profile is a profile defined by an expression that can be transformed (by translation, dilatation (scaling), or some combination thereof) into a standardized normal frequency function $$\varphi(U) \equiv \frac{1}{\sqrt{2\pi}} e^{-\frac{U^2}{2}}, \quad (6)$$

where U may be some function of one or more independent variables.

The expressions (2)-(5) together define a family of two-dimensional Gaussian profiles based on elliptical level sets. That is, at each brightness value in the range of F, the points on the profile lie on a plane ellipse centered at $(a_4, a_5)$. The major and minor axes have lengths $a_2$ and $a_3$, respectively, and are rotated $a_6$ radians in the positive direction from the x axis.

It has been found that 2D Gaussian profiles effectively model the pixel brightnesses of lumen regions in cross sectional images of vessels. Potentially useful classes of functions for profile fitting in the present invention may also be adapted from other frequency distribution functions, such as the Student's t distribution and (in some cases) the $\chi^2$ distribution.

Because the pixel data elements of the image data are discrete data values, it may also be possible to use discrete probability distributions, such as the binomial distribution and the Poisson distribution, to model the brightness contour of an image feature. Of course, the image data to be modeled through the profile fitting operation have important distinctions from a typical statistical data sample, as discussed above. The present invention accordingly permits the selected family of profiles to be based on a statistical frequency distribution function, and also may be practiced with any other family of profiles corresponding to the pixel data contours of the image data.

It is noted that the assumption of elliptical level sets correlates reasonably well with the shape of the residual lumen 630 in FIG. 6. The present invention can accommodate such geometrical features of the structures of interest to an extent not possible with previously existing approaches. For example, quantification of stenosis by measuring diameters either requires measurements in several non-parallel image planes, or else assumes that the residual lumen is substantially round. A method embodying the present invention can account for the actual geometrical features of the structure and so can more effectively extract quantitative information from the available image data.

The fitting operation 932 selects a profile, such as a two-dimensional Gaussian profile, that fits the image data of the lumen region. Any of various optimization criteria may be applied to fit the profile according to well known fitting techniques, such as linear least squares, nonlinear least squares, spatial warping, curvature minimization, and so forth. For example, a computer program in a suitable programming language may be easily prepared to fit a profile from the family of profiles defined by expressions (2)-(5) above. Numerous commercially available programming languages and environments for data visualization and analysis are well known to those of skill in the art and may be used by a programmer of ordinary skill to prepare such a program. Accordingly, the particular details of such programs will be omitted here.

The profile selected through the profile fitting operation 932 is typically represented by one or more numerical values that provide values for the parameters of the selected family of profiles. One, some, or all of the parameters are selected in an operation 942. The values of the selected parameters are to be used in computing the desired measurement of the extensional feature of interest (here the lumen cross sectional area).

The operation 942 may be performed in advance of analyzing the particular image data, if the feature of interest has a known relationship to the parameters of the selected family of profiles. In the above-noted embodiment based on the expressions (2)-(5), for example, it has been found that the values of parameters $a_2$ and $a_3$ can provide a reliable estimate of the residual area of the lumen. In such a case the selected parameters can be identified by expressly coding a computation using values of those parameters.

Other combinations of parameter values may also be used to provide the desired measurement, based on the type of the extensional feature to be modeled and the family of profiles selected for fitting the image data. Further, depending on the circumstances, it may be desirable in such cases to perform the identifying operation 942 after the profile fitting operation 932 has generated a selected profile for the image data.

Based on the identified parameter values, an estimate of the lumen area for the axial position of the slice image is computed in an operation 952. In the particular embodiment noted above, the area estimate was computed as the product $a_2 \cdot a_3$.

The above description has presented the specific case where the profile fitting operation fits a Gaussian surface with elliptical level sets to the input image data. It will be appreciated that even such an exemplary embodiment of the invention could be adapted to estimate areas of other image features of a known type. To achieve such an adaptation, the implementation of the invention might be modified to replace the family of elliptical Gaussian profiles with another family of profiles from which a particular profile would be fit to the image data. The other family of profiles would be selected to model a characteristic shape of the image features of interest.

The procedure of FIG. 9 thus produces an estimate A(i) of the lumen cross sectional area at the axial position x(i) of the slice image. On the other hand, as noted above, the accepted wisdom in the art has been that any measurement from an image of a vascular cross section has relatively little value for assessing stenosis of the vessel.

Two reasons have been thought to exclude the possibility of using cross sectional images to assess vascular stenosis. First, the known approaches for assessing stenosis from such an image would entail some sort of thresholding and image segmentation. Such approaches would make the quantitative results dependent on image noise, image artifacts, and operator-selected parameters (such as segmentation threshold values). The aspect of the invention described above successfully addresses this problem.

But even with a robust estimate of lumen area, a second problem still must be overcome. It is apparent that any cross sectional image merely provides a measurement at a single axial position. The severity of vascular stenosis, on the other hand, should be assessed on the basis of the greatest extent of lumen narrowing along the affected vessel. This fact has been thought to require longitudinal slice images, because no other technique has been available to identify the location at which the lumen is most narrowed. Thus, it has been understood that cross sectional images of vessels are relatively useless for assessing stenosis.

The present invention therefore provides, in a further aspect, an approach that proceeds against the conventional wisdom of the art, yet successfully produces accurate quantitative assessments of arterial stenosis. Generally, this aspect of the invention allows a spatial characteristic of a structure within the imaged object to be quantified, based on three-dimensional tomographic image data representing the structure. Here, a "spatial characteristic" is a property of the structure that may vary between different locations in the structure or may be determined by the overall geometry of the structure or a relevant portion thereof.

A particular embodiment of this aspect of the invention will now be described with reference to FIGS. 10-11. In this embodiment, the structure is preferably a blood vessel of a human patient and the spatial characteristic of the vessel is the degree of stenosis therein.

Figure 10:
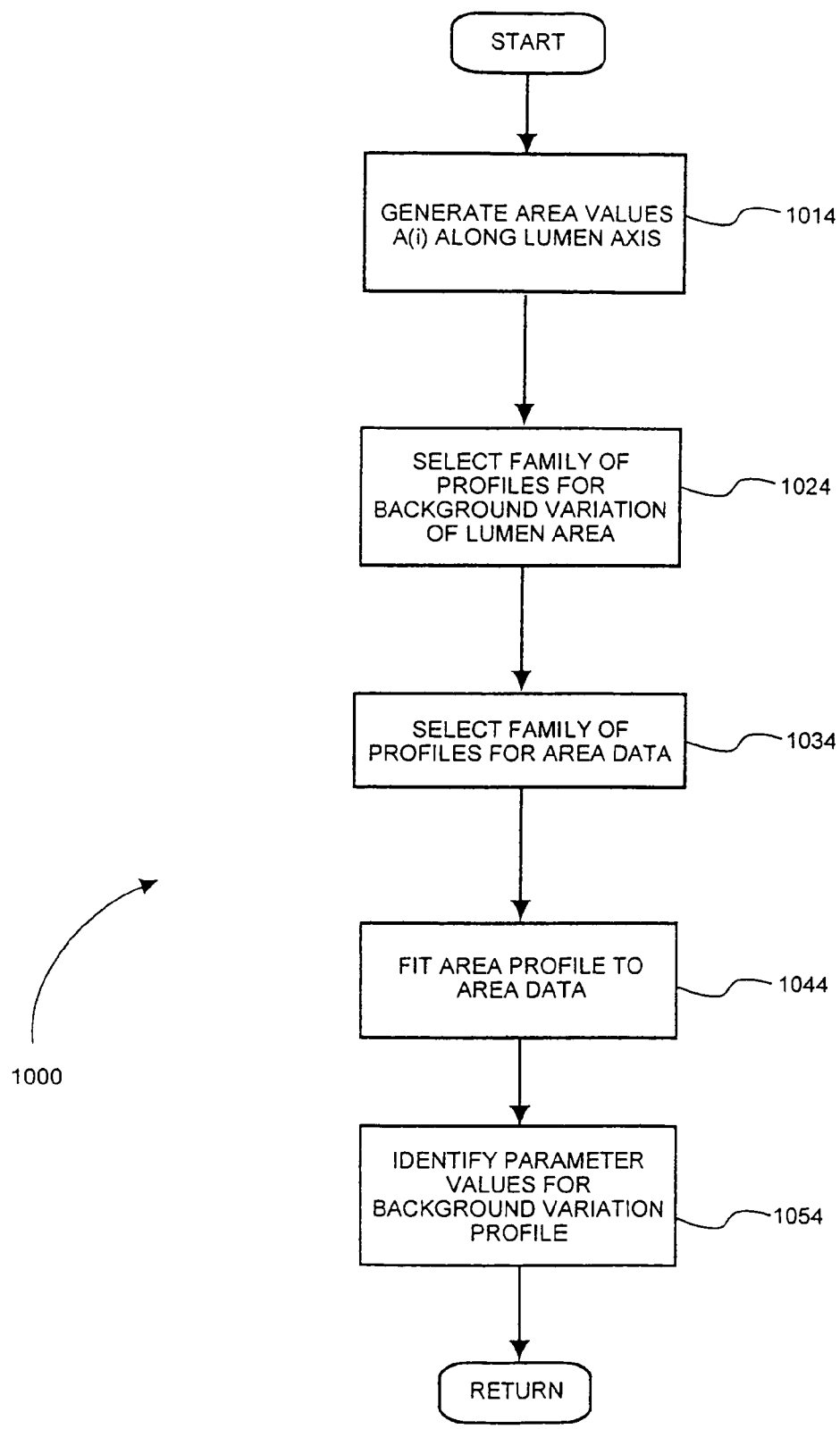
FIG. 10 is a flow diagram illustrating a procedure for use in another aspect of the invention.

FIG. 10 shows a flow diagram illustrating a procedure 1000 for a first phase of this further aspect of the invention. An operation 1014 generates a plurality of area estimates A(i) at corresponding axial positions x(i) along the longitudinal axis of the vessel. In a preferable embodiment, each area value A(i) is generated by a feature measurement procedure of the present invention, such as the procedure illustrated in FIG. 9.

The result of operation 1014 is a set of area values that can be plotted as a function of position along the longitudinal axis of the vessel. A naïve approach would simply read off the smallest area value from such a plot. Unfortunately, it has been found that assessment in such a direct manner may be difficult because the plot of the area values A(i) may itself contain a significant noise component.

An embodiment of the invention also solves this further problem by including operations for modeling the area plot with one-dimensional profiles. An operation 1024 selects a family of profiles by which to model the background (i.e., normal) variation of the lumen area along the axis. For example, in a particular embodiment it was assumed that the normal size of the vessel (e.g., an artery) changed gradually along the region of interest. This assumption merely reflects the fact that real vascular structures are generally not perfectly cylindrical in shape.

A family of low-order polynomial profiles can be selected in the operation 1024 for modeling the background variation of the lumen area. For example, in the particular embodiment noted above, the family of second-order polynomials was selected. It is useful to bear in mind that the desired result of the overall procedure is an estimate of the extent to which the actual area diverges from the (normal) background variation.

In the usual case of gradual background variation, a family of low-order polynomials can be expected to provide an effective model for the background variation. It is therefore possible, as an alternative implementation, for the background variation model to be selected in advance, either at an initial stage of the procedure or even predetermined for the image data analysis. In a particular embodiment of the invention, the family of second-order profiles may be predetermined.

An operation 1034 selects a family of profiles with which to model the actual area data A(i). To capture both the background variation and any divergence therefrom, this second family of profiles is selected based on the background family. It is preferable to select the second family as a superposition (i.e., sum) of the family of background profiles (operation 1024) and another family of profiles selected to model the variation from background.

Thus, in a particular embodiment, the operation 1034 may select the family of profiles defined by second-order polynomials plus one-dimensional Gaussians:

$$A_L \equiv p(x) + g(x), \quad (7)$$

where $$p(x) \equiv b_0 + b_1 x + b_2 x^2, \text{ and} \quad (8)$$

$$g(x) \equiv b_3 e^{-\frac{1}{2}\left[\frac{x-b_4}{b_5}\right]^2}. \quad (9)$$

Here $b_0$, $b_1$, $b_2$, $b_3$, $b_4$, and $b_5$ are parameters of the selected family of area profiles.

An area profile from the selected family of one-dimensional profiles AL is fit to the area data A(i) in an operation 1044. This fitting operation is analogous to the fitting operation 932 of FIG. 9, and thus any of various fitting criteria may be used as noted above. It is desirable that the fitting criteria be chosen to be appropriate for the one-dimensional area data and the selected family of area profiles. In a particular embodiment, it may be convenient to use one of various predefined curve fitting routines, such routines being provided in many equivalent commercially available software packages for data analysis. Such a predefined software function may, for example, fit the sum of a Gaussian and a second-order polynomial to the supplied data and may thus be convenient when the area family is selected according to the formulas (7)-(9) above. The result of operation 1044 may thus comprise a set of parameter values defining the selected profile.

Using this set of parameter values, an operation 1054 identifies the values of the parameters associated with the background family of profiles. In a particular embodiment, the operation 1054 thereby identifies a particular second-order polynomial profile $P_B$ that represents the background variation of the area values A(i). $P_B$ is defined by the identified values of the parameters $b_0$, $b_1$, and $b_2$.

Figure 11:
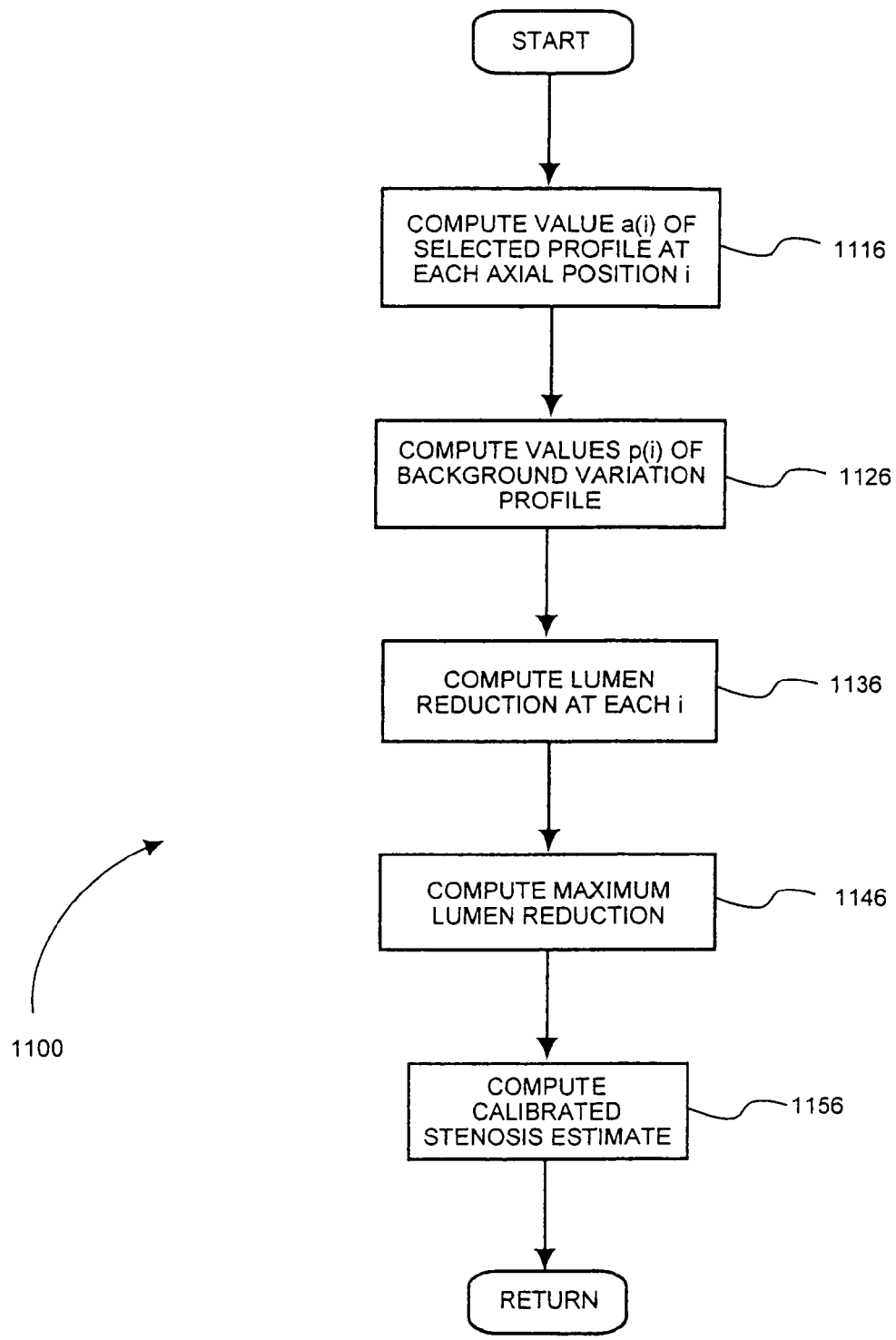
FIG. 11 is a flow diagram illustrating a further procedure for use in the other aspect of the invention.

FIG. 11 is a flow diagram illustrating a procedure 1100 of the present invention for generating an estimate of vascular stenosis based on the parameter values generated in the procedure 1000 of FIG. 10. For each axial position x(i) corresponding to an area value A(i), an operation 1116 computes the value $A_L(x(i))$ determined by the selected area profile. In the particular embodiment, for example, the parameter values generated in the procedure of FIG. 10 and the values x(i) are substituted into the formulas (7)-(9). Alternatively, the actual estimated area values A(i) may be used for the values $A_L$.

An operation 1126 similarly computes values of the background profile $P_B$, which is defined by the parameters $b_0$, $b_1$, and $b_2$ that were identified in the operation 1054 of FIG. 10. The background variation values $P_B(x(i))$ and the area values $A_L(x(i))$ (or A(i)) allow the extent of lumen reduction to be computed in an operation 1136. In a particular embodiment, for example, reduction ratios sten(i) may be computed for each axial position x(i) according to a relative difference ratio such as $$sten(i) = \frac{P(i) - A_L(i)}{P(i)}. \quad (10)$$

The values sten(i) are sorted in an operation 1146 to determine the maximum value sten_max of sten(i) over the axial positions x(i). This value represents an estimate of the maximum relative lumen reduction in the region of interest. Alternatively, the local minimum of the area profile $A_L(x)$ can be determined using elementary techniques of differential calculus (i.e., differentiate, set equal to zero, and solve for $x_{MIN}$). In this latter case the value sten_max may be determined by sten_max=$[P(i)-A_L(x_{MIN})]/P(i)$, where $x_{MIN}$ is the axial position of the calculated local minimum. The value sten_max represents an estimated percent reduction in lumen area at the estimated location of maximum lumen narrowing.

The present invention provides quantitative assessments with the significant advantage of repeatability. On the other hand, it is possible for the resulting estimate of lumen area reduction to contain systematic error arising from the estimation process. It may desirable for the invention to account for such systematic error by a calibration operation 1156. For example, if the percent error is assumed to be constant over a range of computed stenosis estimates, then a recalibrated estimate may be computed simply as sten_recal=$C_R$·sten_max, where $C_R$ is a corresponding recalibration constant.

Alternatively, if the percent error varies with the magnitude of the stenosis estimate sten_max, then the embodiment may desirably use a table of recalibration values to compute sten_recal. A recalibration factor can be selected from such a table based on the value of the estimate sten_max. If the value of sten_max falls between two of the tabulated recalibration values, then an interpolation procedure may be used to determine a corresponding intermediate recalibration value.

A particular advantage of the present invention, when applied in the particular context of medical imaging, is that substantial clinical benefits may be thereby realized. The present invention enables the scanning procedure to be minimally invasive since it is necessary to inject a contrast medium only peripherally in the venous vasculature to properly assess stenosis in blood vessels, whereas contrast agents have to be administered proximally in the affected arteries for conventional arterial angiography.

Reformatting Volumetric Data to Aid in Assessment of Image Features

Processed image data may represent a volumetric image of the imaged object, and in such case the processed data is referred to as volumetric reconstruction data or "volumetric image data." But once the volumetric images have been generated by any imaging modality (such as MRI, CT, ultrasound, etc.), assessment of an image feature from the reconstructed images (e.g., quantification of stenosis) remains difficult. In the case of stenosis quantification, generally a vessel of interest will not be orthogonal to a rectilinear grid used in known reconstruction algorithms. Therefore, an approach for reformatting the volumetric reconstruction data to improve quantification of stenosis in a vessel or other structure is desirable. More generally, it would be desirable to reformat volumetric data to provide images that are better oriented for accurate assessment of structural features represented in the images.

Figure 12:
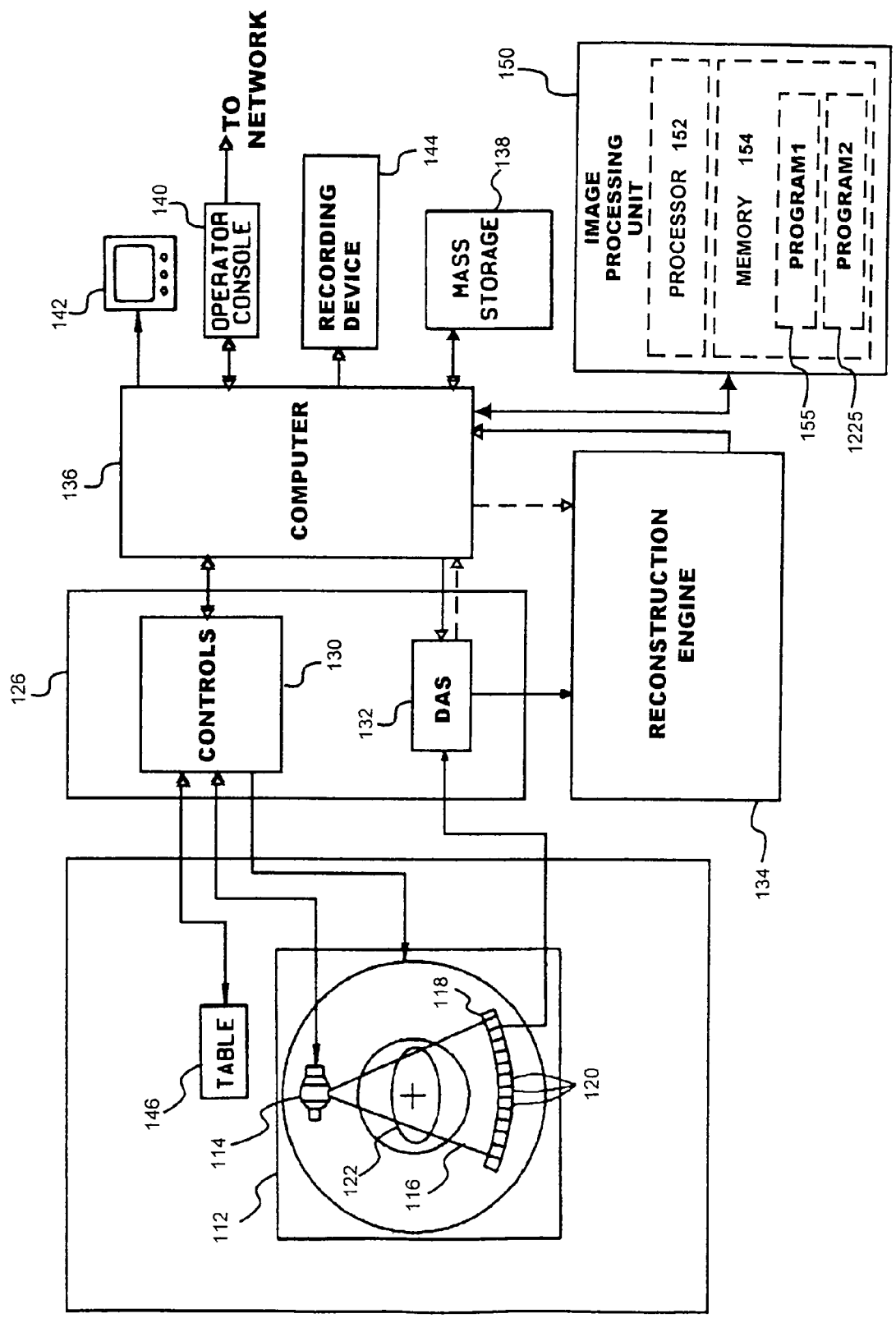
FIG. 12 shows an overview of an x-ray or computed tomography system for use in conjunction with carrying out an embodiment of the present invention.

FIG. 12 shows the imaging system 100 of the present invention with the addition of a second program, PROGRAM2, stored in the memory 154 and denoted by reference numeral 1225. Explanation of the supplemented imaging system 100 as shown in FIG. 12 focuses again on the image processing unit 150, and in particular on the processor 152 and memory 154. For purposes of the present description, the program 1225 will be considered as a software entity distinct from the program 155. Those of ordinary skill will appreciate that programs 155 and 1225 may be embodied in a single software product that will be encompassed within both the present invention for feature quantification and the reformatting technique to be described.

Explanation of the reformatting enhancement begins after the imaging system 100 has acquired volumetric (three-dimensional, or "3D") projection data of the object 122 using x-ray source 114, detector array 118, and DAS 132. Acquiring volumetric data using an imaging system is well known in the art. The projection data are then reconstructed into 3D image data by a suitable reconstruction procedure, as described previously. For purposes of clarity, it is noted that in the following description "volumetric projection data" are two-dimensional projection data representing transmission corresponding to points occupying a three dimensional region of the imaged object and from which a three dimensional image may be generated.

Figure 13:
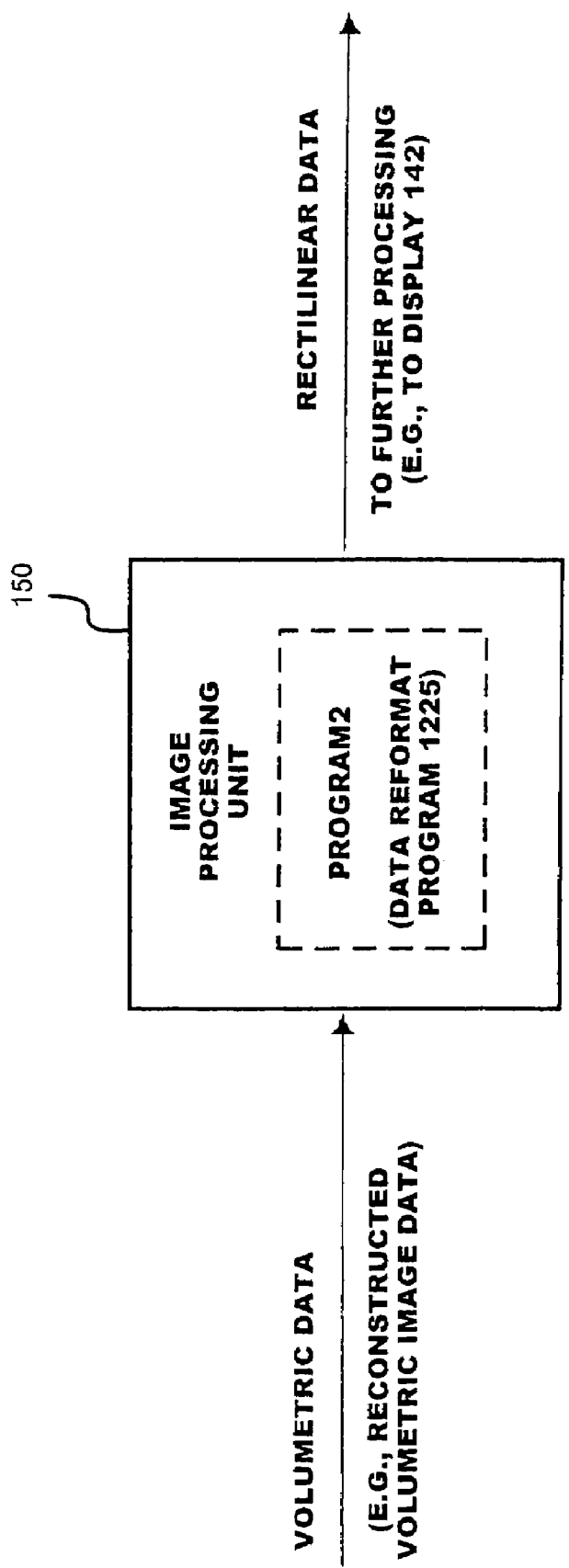
FIG. 13 shows an overview of the data reformat program of the system of FIG. 12.

FIG. 13 illustrates the operation of the image processing unit 150 according to the instructions of the program 1225. Once the volumetric data have been acquired, the CT system image processing unit 150 reads data reformat program 1225 from, for example, non-volatile storage such as mass storage 138 and writes program 1225 into memory 154. FIG. 13 shows that the volumetric data are then input to the data reformat program 1225, and the image processing unit 150 executes the data reformat program 1225. The resulting output of the data reformat program 25 is reformatted volumetric data corresponding to the object 122.

In the following description, "sectional image data" are data specifying a cross sectional image, i.e., a two dimensional image of a cross section of a three dimensional object. Sectional image data will sometimes be called "rectilinear data" or "rectilinear image data." Moreover, a set of data "specifies" an image when the image can be displayed or reproduced from the data set. An "image data set" is such a set of data specifying an image. An image data set may specify a two dimensional image or a three dimensional image.

Figure 14:
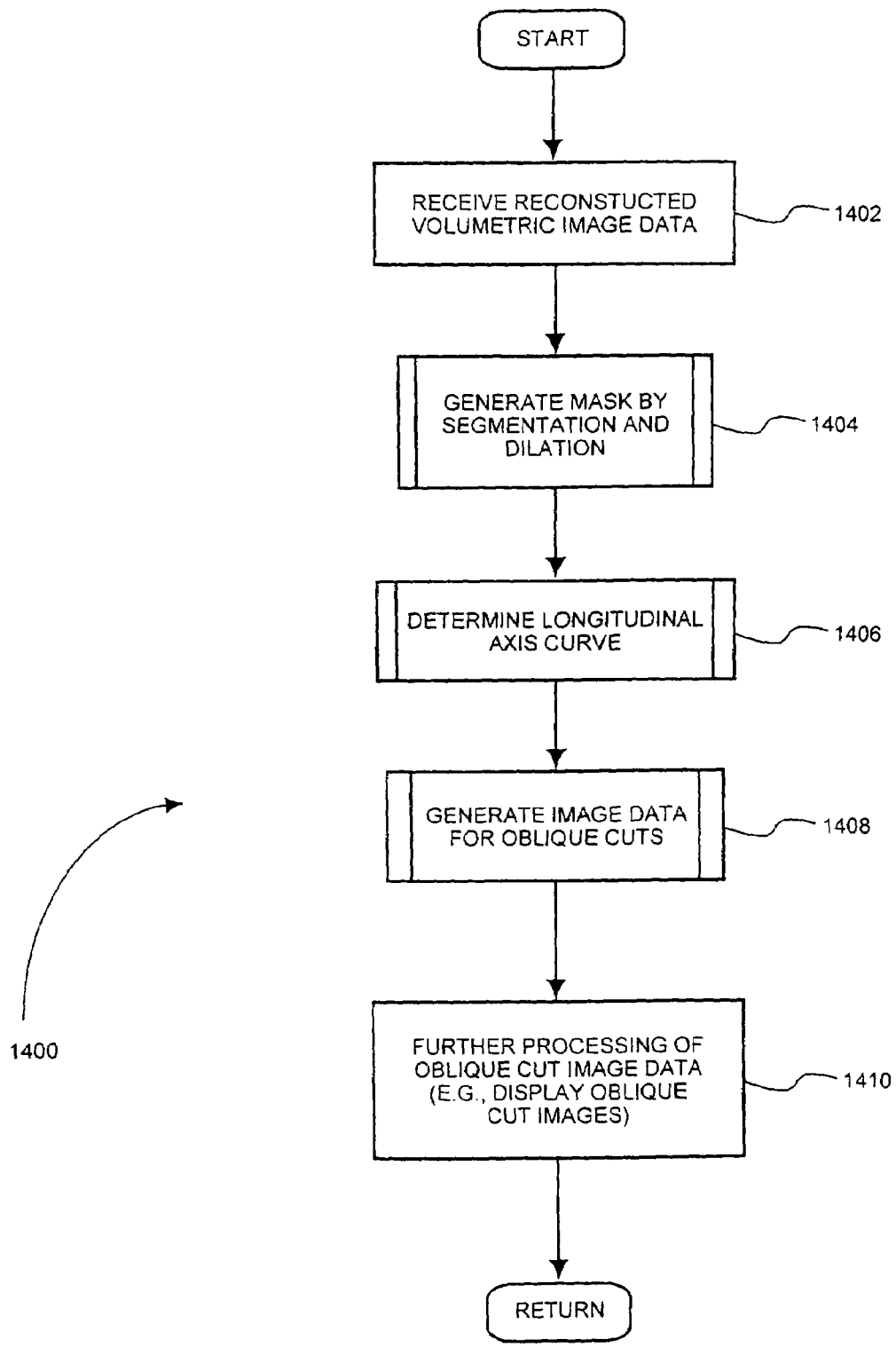
FIG. 14 shows a flowchart of a method for use in conjunction with carrying out an embodiment of the present invention.

FIG. 14 is an overview of the data reformat process 1400 of the present invention which the data reformat program 1225 of FIG. 12 directs the image processing unit 150 (or the system computer 136, or the reconstruction engine 134, depending on the particular implementation) to execute. The data reformat process 1400 is explained in further detail with reference to FIGS. 15-23.

Referring now to FIG. 14, volumetric image data, once reconstructed using standard techniques appropriate to the given modality such as CT, or otherwise obtained by alternative imaging methods, is received in an operation 1402 and input to the data reformat program 1225. The volumetric data may correspond to an image of a complex subject containing longitudinally extending structures therein. Each such structure may include one or more spatially curved portions. Such a longitudinally extending structure may be, for example, any tubular structure. In particular, such a structure may be a fluid-transporting structure such as an animal blood vessel.

In a particular embodiment, such a longitudinally extending structure may be a blood vessel of a human patient. In the latter case, the complex structure may include tissue adjacent to (or "adjoining") the vessel, such as tissue of an organ supplied by the vessel. In the exemplary embodiment to be described, the present reformatting technique is applied in the particular context of imaging of blood vessels. Those of skill in the art will appreciate that the technique applies with equal force and advantage to a broad range of imaging problems where volumetric image data of a complex structure is desired to be reformatted for better examination or assessment of structures such as vermiform structures therein.

As used in this specification, a "volumetric structure" is a physical structure, perhaps comprised partly or wholly in a larger object, and extending in three spatial dimensions. Thus three-dimensional objects are and may comprise volumetric structures, whereas a shadow on a planar surface extends in only two dimensions and therefore is not a volumetric structure. A "section" of a volumetric structure is a two dimensional view of the structure in a specific plane.

A "structural feature" of a volumetric structure is a quantitative dimension or property of the structure. Some examples are here offered for purposes of illustration and are not to be considered as limiting thereto. For example, a structural feature may be the volume of the three-dimensional region occupied by the structure, the length of a characteristic part of the structure, a major axis along which the structure predominantly extends, a minor axis transverse to a major axis of the structure, an area of a surface portion of the structure, and so forth.

A "vermiform" structure is a volumetric structure extending along a longitudinal axis (which may be a curvilinear axis) for a distance at least several times the largest diameter of the structure orthogonal to the longitudinal axis. A portion of a vermiform structure may be referenced as such a structure, even though the portion itself extends longitudinally for a distance less than several times the largest diameter of the structure. A "tubular" structure is a vermiform structure defining an interior void extending substantially along the longitudinal axis. Typically, although not necessarily, the interior void or "lumen" of a tubular structure is a connected region, in which case the tubular structure is topologically equivalent ("isometrically isomorphic") to a torus.

The reformatting process 1400 proceeds with an operation 1404 that generates a mask of a region of interest represented in the volumetric image data and corresponding to a longitudinally extending portion of a vessel. A preferred procedure for this mask generation desirably includes threshold segmentation and dilation operations. The process 1400 continues with an operation 1406, wherein a longitudinal axis curve for the vessel portion is determined from the volumetric mask generated in the operation 1404.

In slightly more detail, once the center, in x,y coordinates, has been determined for each slice containing the vessel along the z axis of the reconstructed volume the x,y coordinates are a function of z, and a least squares fit to the x,y coordinates is developed. Basically, x is a function of z for the x coordinates of the vessel center. Likewise, y is a function of z for the y coordinates of the vessel center. A polynomial is fit to each of these data using least-squares techniques to generate a smooth representation of the axis of the vessel. As a result of the above-mentioned process, a representation of the center line (i.e., the longitudinal axis) to the vessel is obtained. Planes orthogonal to the center line are then computed, and the data on the oblique planes are examined. Pixel values are estimated on the orthogonal planes computed relative to the center line.

An operation 1408 generates image data for oblique cuts along the longitudinal axis curve. Here "oblique cut" means a cross sectional image of the longitudinal extending structure in a plane that has a selected, non-parallel orientation with respect to the three dimensional rectilinear grid on which the volumetric image data are represented. In the particular embodiment to be described in detail, the oblique cuts are selected to be orthogonal to the longitudinal axis curve at respective positions therealong. When two or more oblique cuts are selected, the different oblique cuts may have different orientations with respect to the 3D rectangular grid.

The "orientation" of a cross section is the angular orientation of the plane of the cross section with respect to a predetermined set of orthogonal axes in three dimensions. The orientation of a cross section may be expressed in various equivalent ways. For example, the orientation may be expressed by the coefficients of the linear equation of the plane in three dimensions, i.e., $Ax+By+Cz+D=0$. Alternatively, the orientation may be expressed in terms of the unit normal vector to the plane.

A plane is "selected" by specifying a position and an orientation for the plane. It is a well known fact of geometry that a given vector in three dimensions is sufficient to specify a family of parallel planes having a common unit normal vector parallel to the given vector. Accordingly, a particular plane may be selected by, for example, specifying (1) a point to be included on the plane and (2) specifying a line to which the plane is to be orthogonal. Preferably the specified line also passes through the specified point, but this is an optional arrangement. Those of skill in the art will appreciate that the oblique cuts may alternatively be selected with other orientations relative to the axis of the structure.

The process 1400 also desirably comprises an operation 1410 for further processing of the reformatted volumetric image data on the (one or more) oblique cuts. For example, display of the images of the oblique cuts, as provided by the reformatted image data, is a frequently used post-processing operation. Image display is well known to be a conventionally preferred post-processing modality for assessment of imaged structures, particularly for medical images. Other post-processing operations are also possible, such as computational processing of the reformatted image data to generate quantitative results.

The operations 1404-1408 of FIG. 14 will now be described in detail and with reference to FIGS. 15-17.

Figure 15:
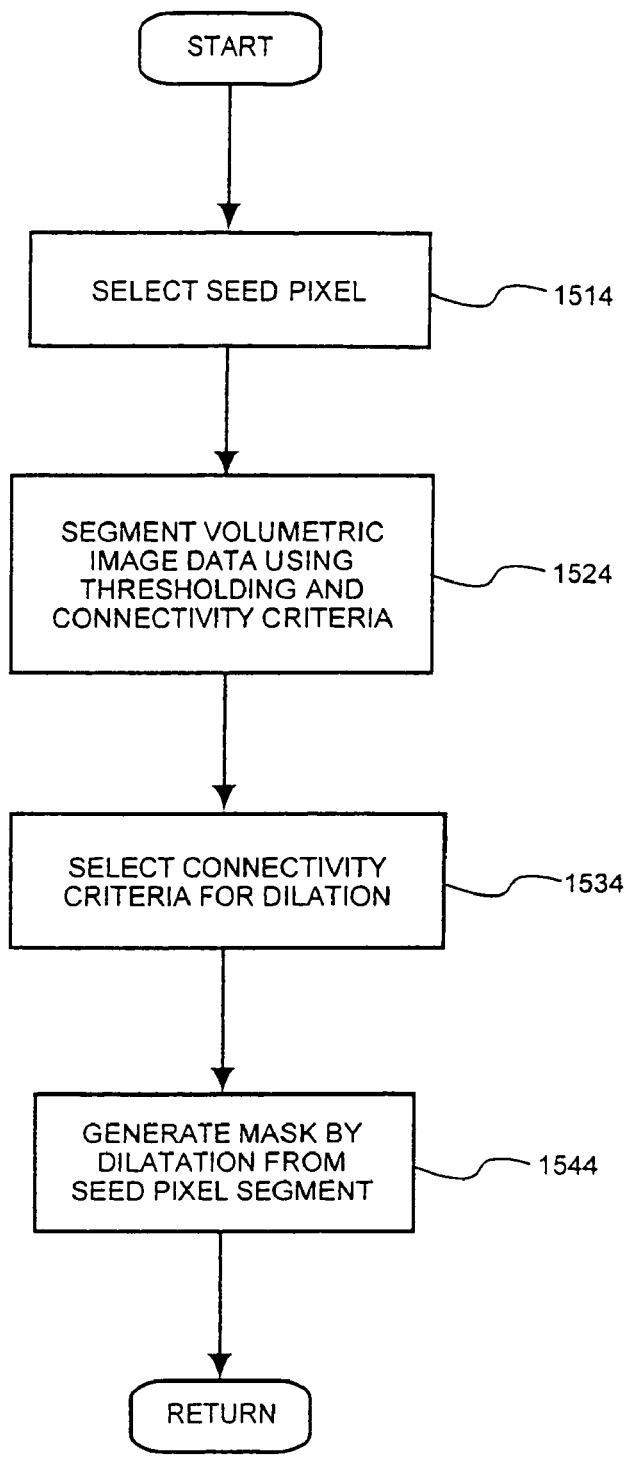
FIGS. 15-23 show detailed processes of the method of FIG. 14.

FIG. 15 is a flow diagram illustrating an exemplary procedure for carrying out the operation 404 of FIG. 14. In FIG. 15, a so-called seed pixel is selected in an operation 1514. Here a "seed pixel" is a pixel of the volumetric image data confidently known to be included in the region of interest. For example, in the context of vascular imaging to assess stenosis, a seed pixel may be a pixel known with high confidence to be included in the vessel lumen. The seed pixel is desirably determined from an operator input, such as a cursor designation with respect to an image from the initial, rectilinear grid image data. Alternatively, the seed pixel may be designated in advance from a preliminary analysis of the initial volumetric image data.

The seed pixel is used to perform a rough segmentation of the volumetric image data by a thresholding procedure that requires the pixels to be connected, in an operation 1524. The rough segmentation of operation 1524 provides an initial determination of the region of interest but is desirably designed to exclude marginal pixels. A more precise categorization of the pixels is then performed from the rough segmentation results, using morphological operations, which use connectivity criteria selected in an operation 1534. A so-called mask of the region of interest (e.g., the vessel lumen) is then generated by morphological dilation of the rough segment in a dilation operation 1544.

The seed pixel of operation 1514 provides a starting point from which the pixels of the initial image data are "segmented," i.e., divided into pixels of the region of interest and pixels of other regions. The region of interest (e.g., the vessel lumen) is first partitioned roughly in a threshold segmenting operation 1524. The vessel interior is roughly designated by segmenting the vessel from the remaining tissue using a CT number threshold selected based on the distribution of the initial image pixels. Generally, the desired outcome of the segmenting operation 1524 is to distinguish regions of high intensity pixels from regions of relatively lower intensity pixels, or vice versa. The result of the segmenting operation 1524 is a roughly segmented lumen portion, which may also be called a "seed pixel segment." As part of this process, connectivity criteria are applied to the pixels meeting the threshold criterion. As will be appreciated by those of skill in the art, the connectivity criteria ensure that pixels that are not proximate to the seed pixel segment are not included in the output of the segmentation process.

The threshold number is desirably selected by the user such that the vessel can be segmented from the adjoining material (e.g., organ tissues) while maintaining a continuous path along the length of the imaged portion of the vessel. More particularly, a point within the vessel is selected and threshold limits are selected to segment appropriately the vessel (such as an artery) from the remaining tissue (including structures in an organ supplied by the artery, for example) as described above. When the threshold is selected as a large fraction of the maximum pixel brightness in the lumen, regions outside the lumen are excluded by the rough segmentation operation. On the other hand, the threshold is also preferably selected to ensure that the rough lumen segment is continuous along the imaged portion length. Thresholding operations and connectivity criteria to achieve such rough segmentation results are well known to those of skill in the art.

The seed pixel segment desirably provides a starting point for a more precise segmentation of the initial image data. Because the rough segmentation of operation 1524 is preferably biased toward under-inclusion, the seed pixel segment can be expected to form only a part of the region of interest. The operation 1534 of FIG. 15 therefore selects criteria for connecting additional pixels to the seed pixel segment. The selection of these connectivity criteria in operation 1534 may be performed in advance of the other operations of the present invention. The particular criteria may be selected in view of geometrical features of the region of interest, as will be appreciated by those of skill in the art.

The roughly segmented vessel (i.e., the seed pixel segment) is dilated in the operation 1544. More particularly, the vessel is expanded using a dilation morphological operator to ensure that residual contrast-enhanced blood is included in the segmentation of the vessel. In addition, dilation of the vessel (to include more volume than was previously included) minimizes the impact of image artifacts on quantitative analysis of the resulting reformatted image data (if quantitative analysis is to be performed). The vessel surface determined by thresholding techniques may be irregularly segmented if image artifacts exist. The dilation operation tends to mitigate these effects, thereby allowing for more accurate quantitative results from the sectional rectilinear data.

To be added to the region of the seed pixel segment during the dilation process, the pixel of interest, viewed as a 3D rectangular box, must touch the existing region—either along an edge of the box, or along the side of the box, or along a vertex of the box. The connectivity criteria may be any combination of the aforementioned three choices. As part of the operation 1544 of FIG. 15, therefore, a dilation morphological operator is applied to the results of the segmentation operation 1524, using the connectivity criteria selected in the operation 1534.

The dilation morphological operator adds more pixels to the region based on the selected connectivity criteria. For instance, suppose that the condition to dilate the region is that a pixel can be added to the original region as long as is has edge, face, or vertex connectivity with at least one pixel already in the region. By applying the morphological operator, the pixels throughout the volume are analyzed to determine whether they meet the criterion. If so, the pixels are added to the region. More about these and other morphological operators is given in *Fundamentals of Digital Image Processing*, by Anil K. Jain, Prentice Hall, Englewood Cliffs, N.J., 1989, pp. 384-390.

The operation 1544 may apply the dilation operator a selected number of times to generate a mask of the lumen region. Typically a mask is a pixel pattern that can be used to selectively control the retention or elimination of portions of another pattern of pixels. Here the "mask" obtained in the operation 1544 is used first as a standardized representation of the lumen cross section, from which moment (centroid) calculations can derive the cross sectional center of mass. The mask is also used later in the more typical manner, i.e., to select the pixels of the lumen region in the volumetric data.

In a particular implementation of the present reformatting technique, the mask generated from operation 1544 is a three-dimensional array corresponding to the pixel array of the initial volumetric image data but having only binary values, i.e., 0 or 1. The mask pixels have value 1, for pixels considered to be in the lumen region, and value 0 otherwise. The mask is thus a binarized representation of the lumen region, as identified by segmentation and dilation.

Figure 16:
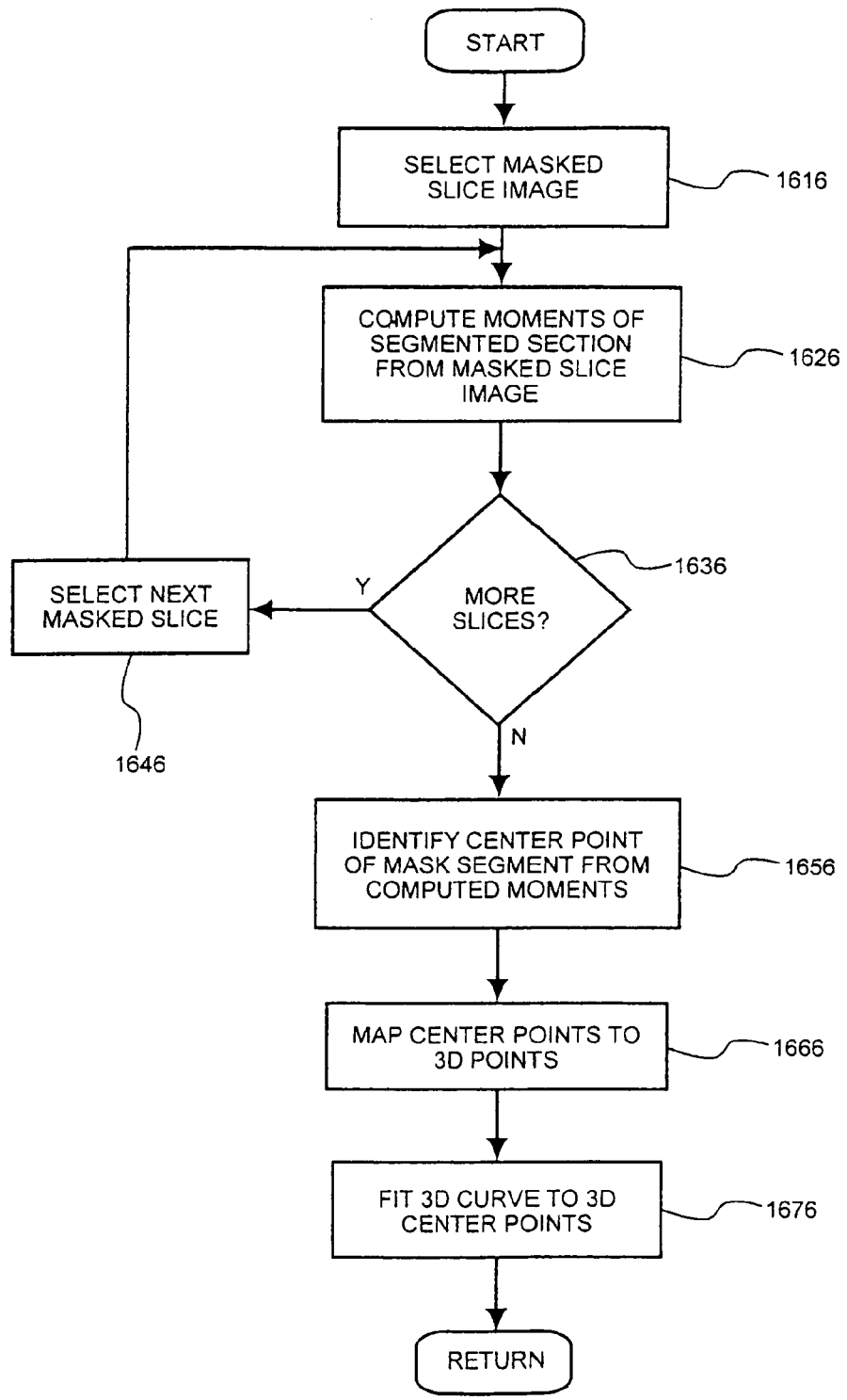

FIG. 16 is a flow diagram illustrating details of a particular embodiment of the operation 406 of FIG. 14. The procedure of FIG. 16 is for determining the longitudinal vessel axis along the entire length of vessel portion represented by the initial volumetric data. Determining the vessel axis is accomplished by using successive slice images from the mask obtained by the procedure of FIG. 15, i.e., "masked slice images." The initial volumetric data represent a succession of slice images (or "axial slices") of the imaged object at corresponding successive image planes defined by the grid points of the rectilinear grid. In the following discussion of FIG. 16 it will be assumed that the two dimensions in each successive image plane are defined by the x-axis and the y-axis, while the succession of axial slices extends in a third dimension defined by the z-axis.

A masked slice image is selected initially in an operation 1616. For each of the x-axis and the y-axis, the moment of the vessel lumen area is computed in an operation 1626 and chosen to be the center of the vessel. More particularly, the center of the vessel is determined by performing a moment calculation on the binary representation of the vessel cross section as provided by the mask, on a slice by slice basis.

An operation 1636 determines whether the mask includes additional slices for which the moments are to be calculated. If so, then an operation 1646 selects the next masked slice image and the procedure returns to the moments computation of operation 1626. Because the mask is a binary representation, for each axial slice the moments (centroids) of the entire masked slice image equivalently represent the moments of the lumen area represented in the slice. It is noted that if more that one vessel occurred in the axial slice, the masked region would be smaller so that the computed moments would relate to cross sections of a single vessel.

When the moments have been computed, the procedure advances to an operation 1656 where the computed moments are used to identify the x-coordinates and y-coordinates, respectively, of the center points of the lumen in each slice image. Thus, a center point $(x_c, y_c)$ is defined for each axial slice by setting $x_c$ equal to the x-moment and $y_c$ equal to the y-moment. The operations 1626 and 1656 may be implemented with a single set of computations, such as $$\text{for } i = 0, \text{nSlices} - 1 \text{ do begin}$$
$$t = \text{mask}(*, *, i)$$
$$tt = \sum_j \sum_k t(j, k)$$
$$xcent(i) = \sum_k \left[ \sum_j t(j, k) \cdot x_j \right] / tt \qquad (11)$$
$$ycent(i) = \sum_j \left[ \sum_k t(j, k) \cdot y_k \right] / tt$$
$$\text{endfor}$$

These are preferably implemented in a suitable object code optimized for the particular processing architecture of the image processing unit 150. It will be appreciated that such implementation is a routine programming task that may be carried out in any of numerous functionally equivalent programming languages (C, C++, FORTRAN, etc.) and would involve no undue experimentation, should any experimentation be entailed at all. The result is to sum the weighted 1-pixels in the y-direction to obtain the weighted "mass" in the y-direction. Similarly, the weighted 1-pixels are summed in the x-direction to obtain the weighted mass in the x-direction. The remaining operations are the standard calculations for computing a centroid and are well known in the numerical programming arts.

The two-dimensional center points $(x_c, y_c)$ are then associated with three-dimensional points in an operation 1666. That is, the operation 664 associates the z-axis position of each axial slice with the lumen center point $(x_c, y_c)$ of the slice. The result is a discrete set of points in three dimensions, each point falling on the longitudinal axis of the vessel lumen at a corresponding z-value of the rectilinear grid.

A three-dimensional curve is then fit to the three-dimensional center points in an operation 1676. Using the moments calculated from each slice, the center points of each slice are fit with a smooth curve using least mean squared error metrics (i.e., a smooth curve which minimizes the squared error between the curve and the computed center points). The smooth curve, then, represents the axis of the vessel in three-dimensional space. In a particular embodiment, the smooth curve is a space curve defined parametrically in the x-variable and the y-variable by quadratic polynomials in z.

As noted above, "curve fitting" is a computational procedure for determining, for a given type or "family" of curves, a particular curve that most closely approaches a specified set of points. A "family" of curves is a set of curves specified by a common set of defining expressions in which the coefficients are represented as parameters. A particular curve in the family may be selected specifying particular values for the coefficient parameters. The one or more expressions with unspecified parameters therefore serve as a template function that may be selected in advance. An appropriate fitting operation determines specific values for the parameters, whereby a specific curve is selected (fit to the data) from the given family of curves.

Thus, curve fitting for the particular problem of selecting a space curve fitting a set of points is analogous to profile fitting as described above. It is also possible to define a curve as a combination of piecewise-defined functions. The curve-fitting operation may match the given data by coincidence at specified points (interpolation), or by determining a "best-fit" curve. The optimization criterion for a best-fit curve is preferably least squares minimization but may alternatively be selected from various curve-fitting optimization criteria as are well known in the art.

The model or "family" of curves may be a family of parametric curves defined by low-order polynomials, such as quadratic polynomials or cubic polynomials. Alternatively, the fitting operation 1676 may determine the curve by any of various interpolation procedures such as spline interpolation (cubic splines, etc.) or other interpolation procedures as are well known in the art.

Figure 17:
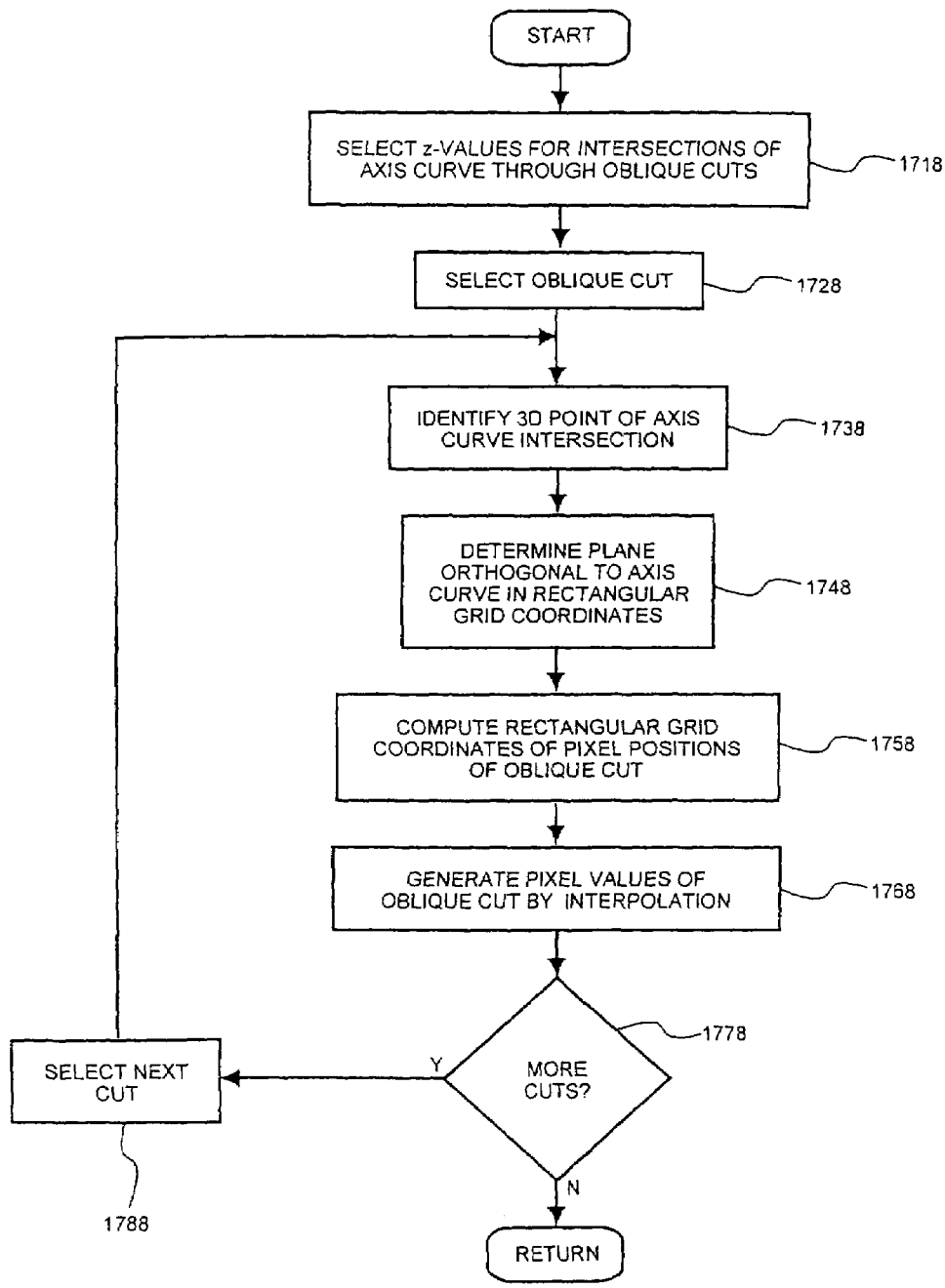

FIG. 17 is a flow diagram illustrating a procedure to implement the oblique-cut generation operation 1408 of FIG. 14. Using the smooth curve, cutting planes at various places are determined along the vessel's longitudinal axis. In a particular embodiment of the invention, the orientations of the planes are selected to be orthogonal to the axis of the vessel. The volumetric data corresponding to the vessel is then reformatted along the cutting planes to generate reformatted CT data as sectional rectilinear data. More specifically, in the particular embodiment the data at every point on each cutting plane that is orthogonal to the vessel's axis is interpolated from the volumetric data, since orthogonal cuts to the vessel correspond to oblique cuts to the volumetric data.

The z-values of the various places are selected in an operation 1718. For example, the selected z-positions can be the z-positions of the successive rectilinear slice images, as determined by the rectilinear grid. It is desirable, but not necessary, to place the axis origin, z=0, nominally at the center of the longitudinal portion of the vessel. Alternatively, the z-values can be chosen such that the distance along the vessel is equally partitioned.

An initial oblique cut is selected at an operation 1728. For each oblique cut, an operation 1738 identifies the three-dimensional point at which the oblique cut is to intersect the longitudinal axis curve. In the case where the z-position of the oblique cut is the z-position of one of the rectilinear grid planes, the intersection point will simply be at or near the three-dimensional center point of the lumen area, as computed in the operations 1626-1656 of FIG. 16.

An operation 1748 determines a selected orientation for the oblique cut, relative to the three axes of the rectilinear grid. In a particular embodiment, the selected orientation places the oblique cut orthogonal to the longitudinal axis curve at the intersection point. Based on the selected orientation, an operation 1758 computes the positions of the oblique cut grid points (i.e., the pixel positions of the oblique cut) in the coordinates of the rectilinear grid.

The selected orientation may be determined by, for example, computing the angles formed by the tangent line at the intersection point, relative to the rectilinear grid axes. Alternatively, the oblique cut orientation may be determined by computing the equation of the plane of the oblique cut. The longitudinal axis curve may be represented by parametric equations defining the x variable and the y variable as functions of z (i.e., z is the parameter). The lumen center points along the curve are determined as outlined above. In this case, at each lumen center point, the unit vector n=(a, b, c) tangent to the curve at that point may be determined readily from the derivatives of x and y with respect to z.

The vector n is, of course, also the unit normal vector to the plane orthogonal to the curve at the particular point. As is well known, the equation of the orthogonal plane is then $$ax+by+cz+d=0, \quad (12)$$

where d may be determined by substituting the values of x, y, and z at the center point. The orthogonal plane may be discretized to determine the oblique cut positions at which the rectilinear image data for the oblique cut will be determined from the volumetric image data.

The foregoing two alternatives, as well as others, are well-known methods for determining a plane having a specified orientation with respect to a given curve. The details of any of these alternatives are easily within the ability of an ordinarily skilled programmer to implement in a selected programming language without undue experimentation. Accordingly, for the sake of brevity, such details are omitted here.

The pixel values of the oblique cut pixel positions are generated in an operation 1768 by interpolation from the pixel values of the initial volumetric image data. In an exemplary implementation, the pixel value of each oblique cut pixel may be computed by, for example, trilinear interpolation from the eight nearest neighbor pixel values on the rectilinear grid. If the pixel values of the eight nearest neighbors are denoted $N_l$, l=1, . . . , 8, then the oblique cut pixel value xsection(j,k,i) may be determined as $$xsection(j, k, i) = \sum_{l=1}^{8} \alpha_l N_l. \quad (13)$$

Here the weights $\alpha_l$ are determined based on the separation between the oblique cut point xsection(j,k,i) and the rectilinear grid point having the pixel value $N_l$ and such that $\Sigma_l \alpha_l = 1$. For example, let the eight nearest neighbors on the rectilinear grid define the vertices of a parallelepiped of nominal volume unity. Then the weight $\alpha_l$ may be defined as the fractional volume of the portion of the parallelepiped diagonally opposite the rectilinear grid position of $N_l$, relative to the oblique cut position xsection(j,k,i). This exemplary embodiment of the interpolation calculation will be explained below with reference to FIG. 23.

An operation 1778 determines whether more oblique cuts remain to be determined. If so, the procedure of FIG. 17 advances to an operation 1788, where the next cut is selected, and returns to the operation 1738. If all the oblique cuts have been constructed, the procedure of FIG. 17 ends.

Then, as indicated in the operation 1410 of FIG. 14, the rectilinear data may be displayed. The reformatted volumetric data corresponding to the vessel is the CT image data that would have been reconstructed from the projection data of the vessel had the vessel been pulled straight on the heart. The selected orientations of the oblique slices provide alternative views of the imaged object that provide benefits in such assessment activities as visual examination of the imaged structure or assessment of structural features from the volumetric image data.

The above-mentioned data reformat process 1400 of the present invention dissects, using the data reformat program 1225 of the present invention, the vessel from the adjoining tissue and then stretches the vessel so that the vessel is straight.

One simple method to process the sectional rectilinear data is to sum all the pixels on the planes normal to the vessel axis. This process essentially estimates the volume of the lumen of the vessel at points along the vessel. When considering a 50% area stenosis in a vessel, this method may be more robust than determining the diameter of the vessel from radiographs generated with angiography. That is, because the area metric would ideally have a 50% contrast while the diameter metric would have a 50%/$\sqrt{2}$ contrast, the area metric would be more sensitive to variations in the lumen area. Other assessment approaches, such as by visual assessment or by a computational procedure as described above with reference to FIGS. 1-11, are also possible.

The data reformat process 1400 of the present invention is now discussed in further detail, with reference to FIGS. 18-23. These Figures provide exemplary illustrations of the operations described above with reference to FIGS. 14-17.

Figure 18:
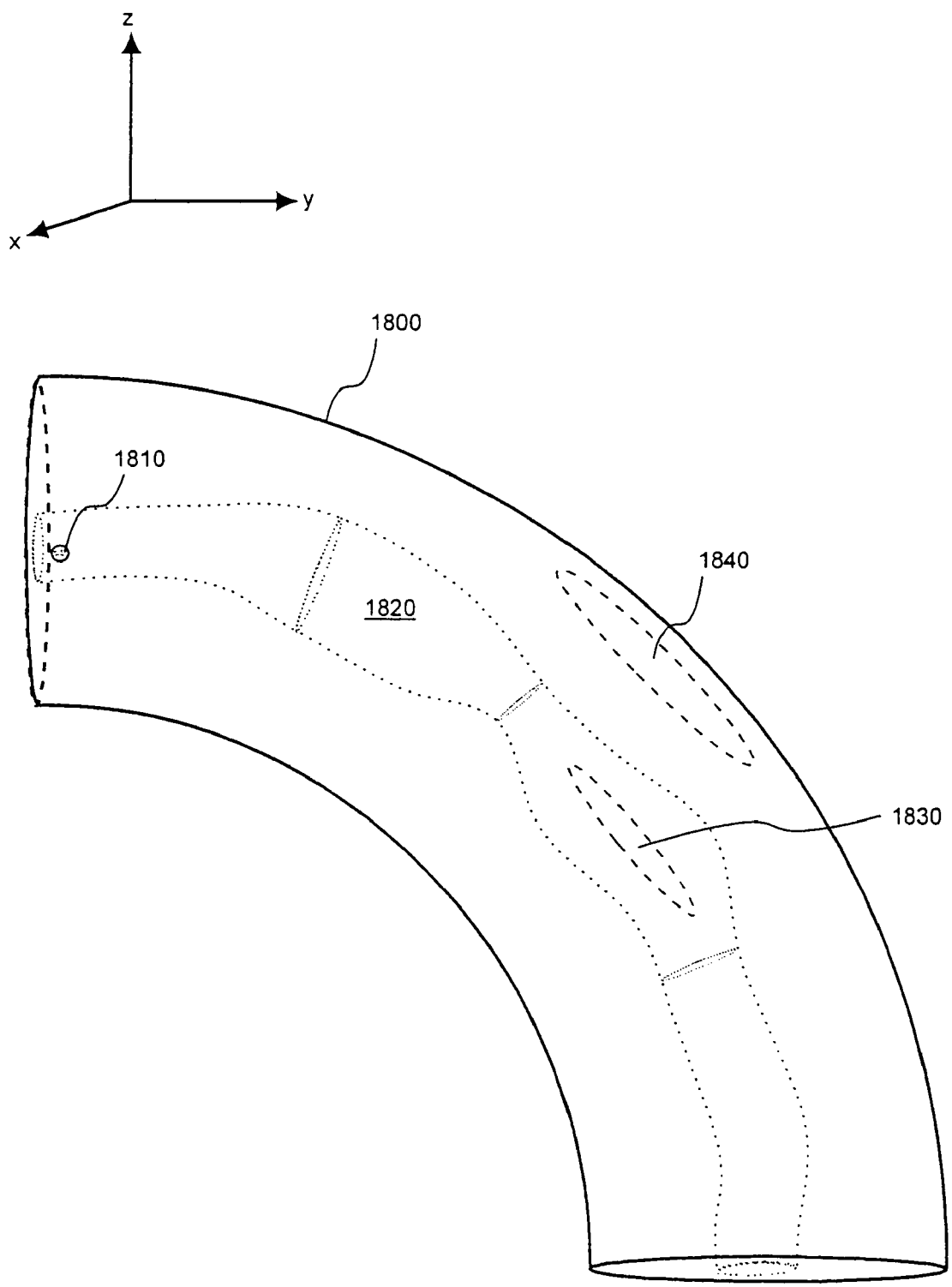

FIG. 18 schematically illustrates a 3D image of a vessel portion 1800 represented by volumetric image data to be reformatted by the invention. With reference to operation 1514 of FIG. 15, a seed pixel 1810 in FIG. 18 is desirably selected from an endmost rectilinear slice of the volumetric image data. The result of the segmenting operation 1524 is a roughly segmented seed pixel segment 1820. As noted above, the desired outcome of the segmenting operation 1524 is to distinguish regions of high intensity pixels, such as region 1830 in FIG. 18, from regions of low intensity pixels such as region 1840.

In FIG. 18 the selection of the threshold number has ensured that the seed pixel segment 1820 extends continuously through the vessel portion 1800. Thus, the seed pixel 1810 in FIG. 18 is used to grow the region of the vessel. The seed is basically a point, optionally a point that a user selects, in the central region of an oblique cross section of the vessel. To grow the region, intensities of pixels above a selected threshold and meeting special conditions are combined as the vessel is traversed.

If a selected pixel is greater than the threshold and is connected to a pixel that is within the region, the pixel is added to the region. In medical imaging applications of the invention, there is typically a finite temporal window for acquiring the volumetric projection data. In such a case, selection of the threshold value (and, therefore, which pixels will be included in the vessel image) is an important consideration. Those of skill in the art will appreciate that a desirable set of criteria for selection of the threshold value will depend on the circumstances in which the projection data are acquired.

More particularly, if a relatively lower value is selected for the threshold value, lower-intensity pixels are included in the image. Lower intensity pixels are typically located at the periphery of the imaged structure, if the structure is tubular, and would be displayed as a roll-off of the structure. Higher-intensity pixels are typically located closer to the center of the structure, which carries the blood if the structure is a blood vessel. Typically, in vascular imaging situations, contrast agents are administered prior to scanning to enhance the detection of the vessels to be imaged.

Figure 19:
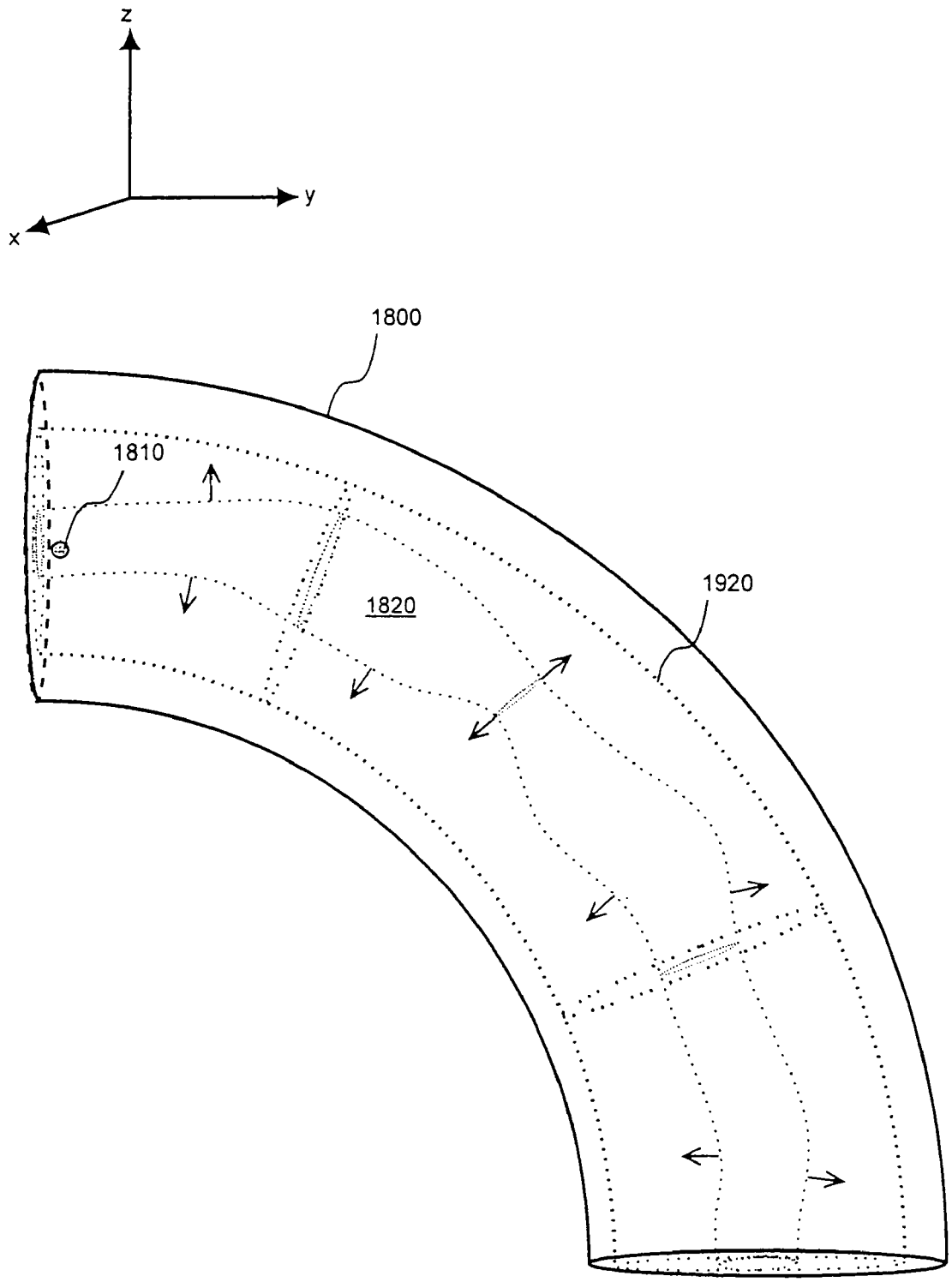

FIG. 19 illustrates the mask generation operation 1544 of FIG. 15. As indicated by the arrows, the dilation operation expands the seed pixel segment 1820 to include more low-intensity pixels. Usually the dilation operation expands the segment 1820 outwardly toward the walls of the vessel 1800. After one or more executions of the dilation operation (e.g., a selected number of times), the expanded segment becomes the mask 1920. The mask 1920 is a binary representation of the lumen region.

Figure 20:
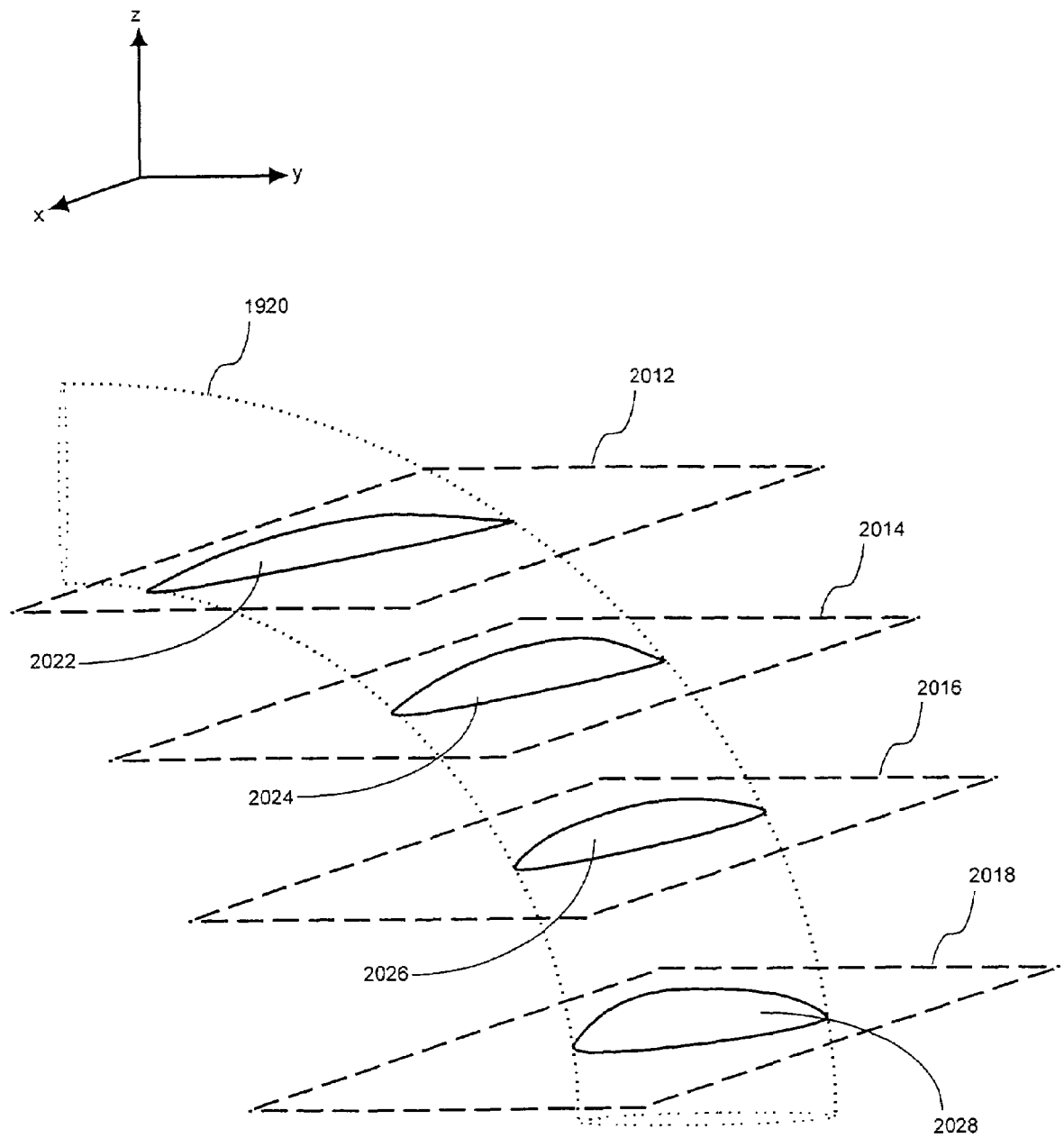

FIG. 20 corresponds to the procedure of FIG. 16. As shown in FIG. 20, the volumetric data corresponding to the vessel forms the basis for, essentially, an image of the vessel in x,y planes 2012-2018, stacked in a z plane relative to the rectilinear grid of the initial volumetric image data. Oblique cross sections 2022-2028 of the vessel, axial scans for the scanner, are then taken, and the center of the vessel is estimated using the oblique cross sections, using moment calculations.

As shown in FIG. 20, the lumen mask 1920 is basically a tortuous cylinder. A tortuous cylinder is one example of a vermiform structure as defined above. Other examples of vermiform structures include right cylinders, tapering cylinders, helicoidal structures, irregular cylinders, etc. The present invention also applies fully to volumetric structures generally.

A rectilinear grid cross section of the vessel, such as cross section 2022, is an oblong or ellipsoidal figure in two dimensions (x,y). The x,y coordinate values of the moment calculation identify the center of the lumen of the vessel at the rectilinear grid cross sections. The rectilinear grid cross sections of the vessel are then used to obtain cross sections that are perpendicular to the longitudinal axis of the vessel, i.e., cross sections in the oblique cuts.

Figure 21:
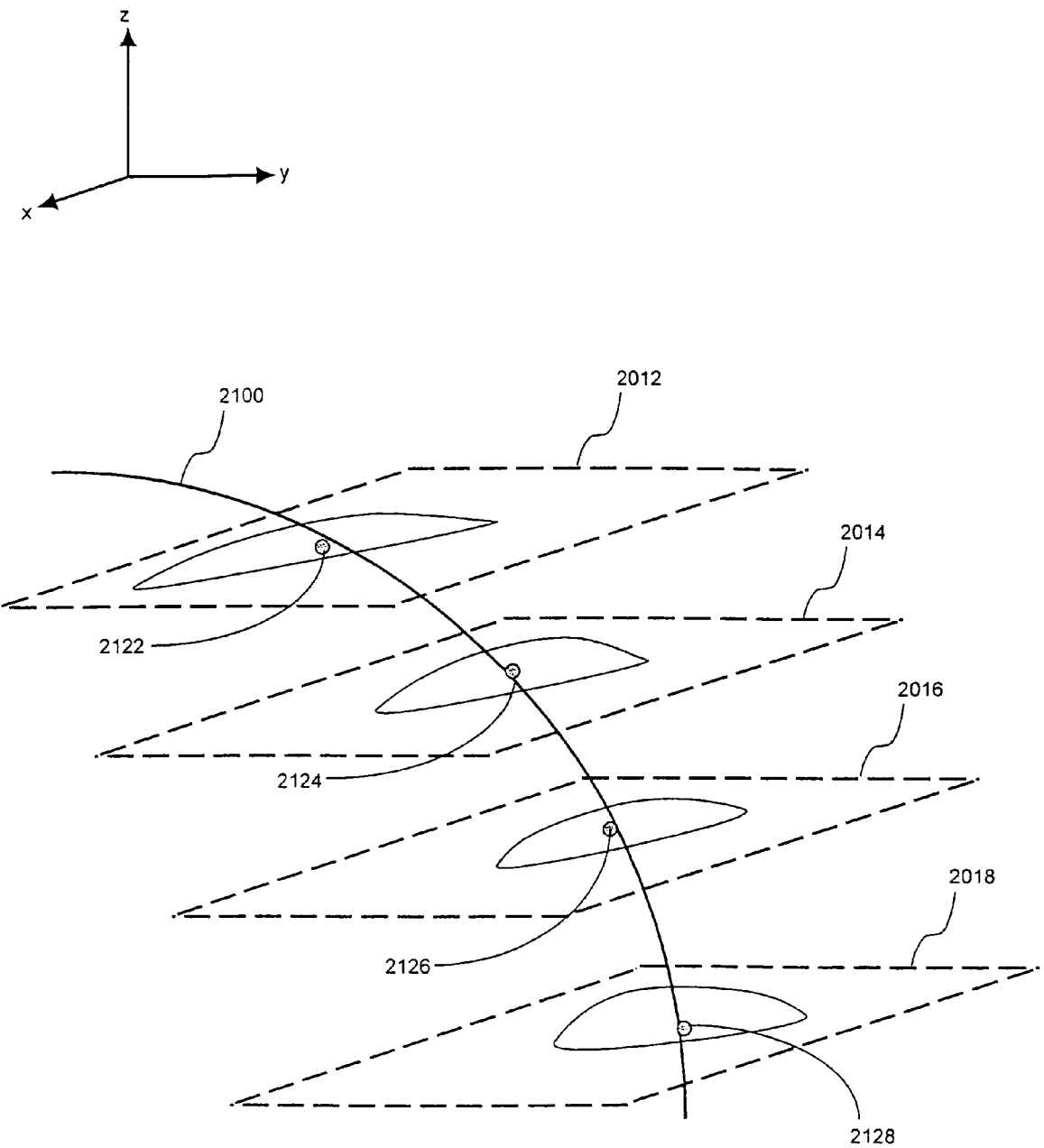

FIG. 21 corresponds to the output of the procedure of FIG. 16 for determining the longitudinal axis curve of the lumen 1920. The three dimensional curve 2100 is the curve fit by the operation 1676 to the center points 2122-2128, which in turn are the centroids calculated in operations 1626-1656 of FIG. 16. As noted above, depending on the particular curve fitting procedure selected for implementation of the method, the curve may not actually intersect the centroid points, unless the operation 1676 fits the curve by an interpolation method such as, for example, spline interpolation.

Figure 22:
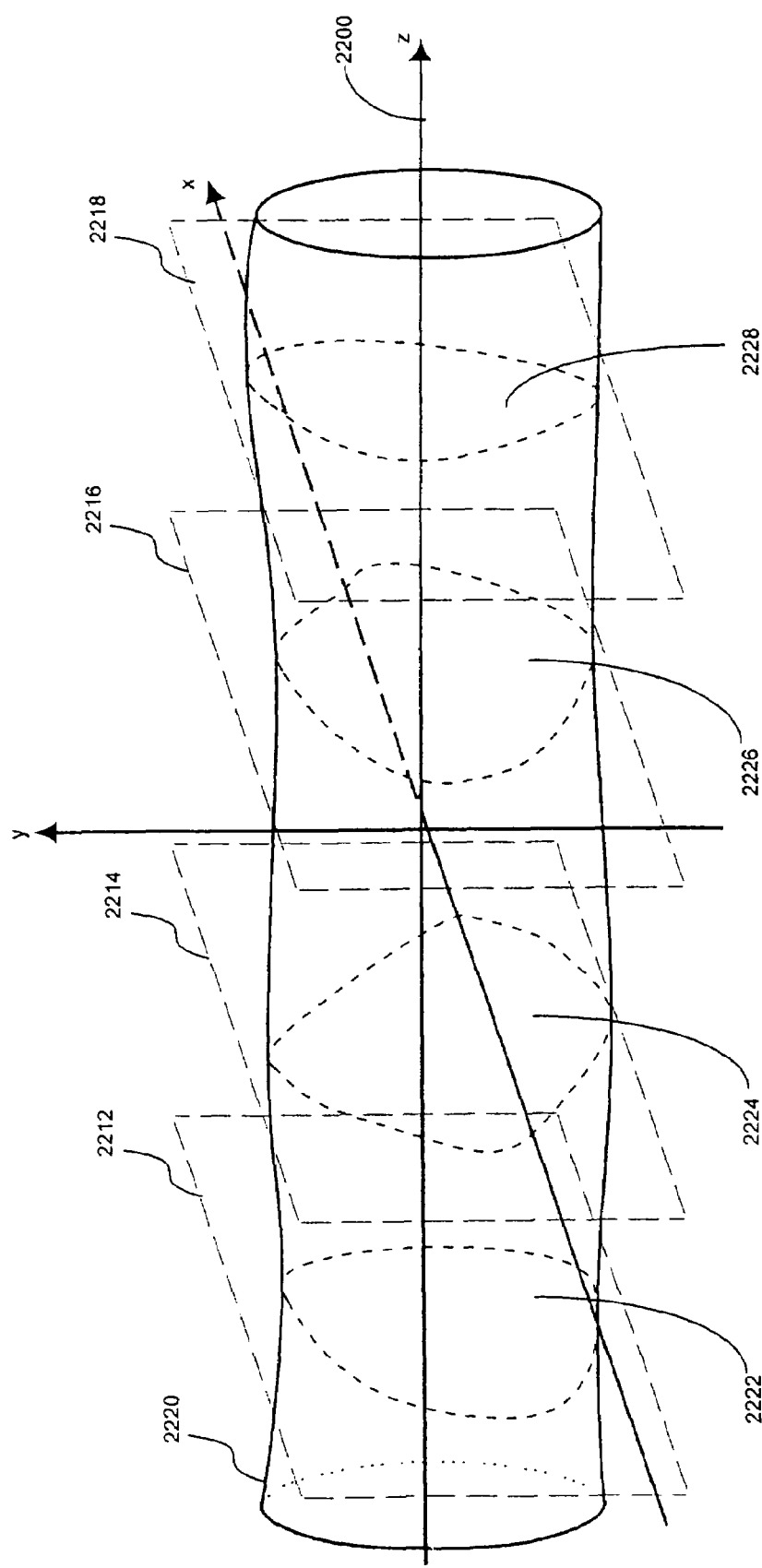

FIG. 22 corresponds to the result of the procedure illustrated in FIG. 17. The z-axis 2200 is the reformatted equivalent of the longitudinal axis curve obtained in the operation 1676 of FIG. 16. The planes 2212-2218 correspond to the planes of the oblique cuts, which are parallel in the reformatted data. The lumen cross sections 2222-2228 represent the cross sections of the lumen in the respective oblique cuts along the longitudinal axis 2200 of the reformatted vessel lumen 2220.

Figure 23:
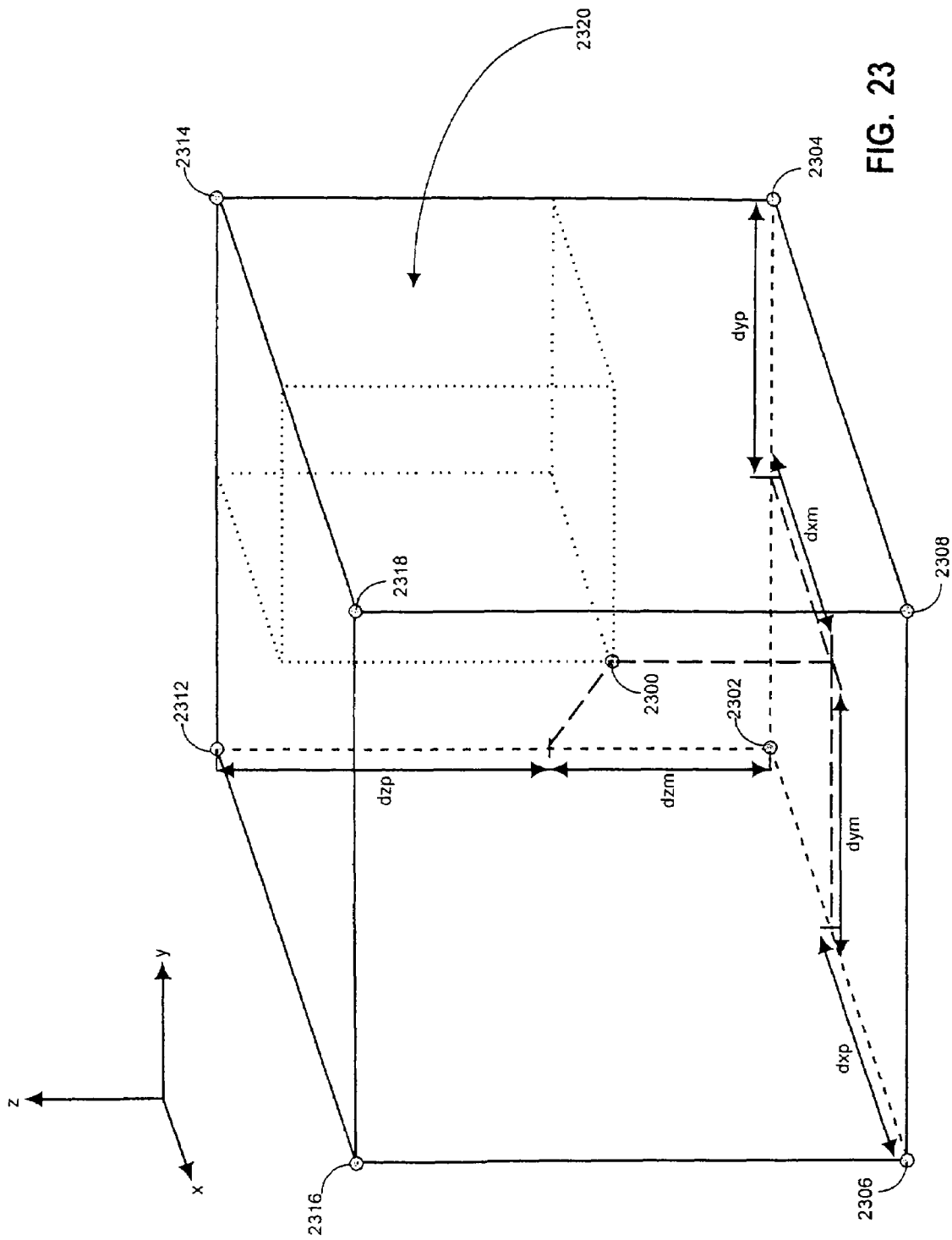

FIG. 23 illustrates the trilinear interpolation carried out in the operation 1768 of FIG. 17. The rectilinear grid spacing in each dimension (x, y, and z) may be normalized to 1. The pixel 2300 is the oblique cut pixel whose value is to be determined by interpolation between the rectilinear grid pixels 2302-2318. The pixel 2302, for example, is at the position (xint, yint, zint) with respect to the rectilinear position of the pixel 2300. The volume element 2320 is diagonally opposite the pixel 2306, which corresponds to the position (xint+1, yint, zint). The volume dxm*dyp*dzp is the interpolation coefficient $\alpha_i$ of the pixel value $N_i$ of pixel 2306, as indicated in the aforementioned description of operation 1768 in FIG. 17.

In a typical case where the present invention is applied in particular to volumetric image data representing a vessel, the data being reformatted may represent a segment of the vessel 6-10 millimeters (mm) in length. Of course, such a vessel in its entirety is generally much longer than the imaged portion.

The foregoing technique for reformatting volumetric data achieves better visualization of volumetric image data, such as three-dimensional tomographic image data, by reformatting the data according to a feature to be visualized. For the case of tomographic image data in particular, an alternative aspect of the technique can also achieve improved visualization by defining the reconstruction planes before performing image reconstruction. The alternative aspect of the reformatting technique, in contrast, uses a back-projection implementation of multi-planar reformation (MPR) to reconstruct a succession of oblique slices as an integrated whole. Moreover, this alternative aspect can capture information from the initial (rectilinear grid) image data to make decisions about the succession of MPR reconstructions.

In simple terms, an embodiment of this alternative aspect may follow the procedure of FIG. 14 above. In this embodiment, however, the operation 1408 comprises multi-planar reconstruction to generate image data for the oblique cuts, instead of employing interpolation on the rectilinear grid image data.

Either of two forms of back-projection may be employed in this aspect of the invention. The goal for each oblique plane is to interpolate between rectilinear grid image data to generate image data for the oblique plane. In a detector-driven approach, each image data volume element (voxel) of the plane is associated with square elements of the detector array. Each square element is back-projected to a point at the x-ray source, thereby sweeping out a tetrahedral volume. If the detector element tetrahedron intersects the voxel, then the detector element's signal is included in the intensity contribution to the pixel of interest. Each included detector signal is weighted by the fractional volume of the voxel intersecting with the detector element tetrahedron.

In a pixel-driven approach, rays are constructed from the source point to the pixel positions in the proposed oblique image plane. For each pixel of interest, the ray is extended to the detector plane to determine a detector plane point. The four nearest detector elements neighboring the detector plane point are identified. Bilinear interpolation is then performed with the signals of the four identified detector elements, using relative distances to the detector plane point to determine the interpolation weights. By repeating this procedure for each pixel in the proposed oblique image, a set of projection data views (i.e., a sinogram) is reconstructed to produce intensity values at sample locations in the oblique plane.

In either the detector-driven case or the pixel-driven case, the details of implementation will be appreciated by those of skill in the art, upon consideration of the above description in conjunction with the aspect of the reformatting technique described above with reference to FIGS. 1 and 12-21. An advantage of the first aspect of the reformatting technique over this alternative aspect is that volumetric image reconstruction may be performed only once (on the rectilinear grid projection data). The back-projection alternative, in contrast, desirably uses information extracted from the rectilinear grid image data to make determinations about the oblique plane positions and orientations (see discussion of FIG. 17, operations 1718-1758).

As this invention may be embodied in several forms without departing from the spirit or principal characteristics thereof, the present embodiments are therefore illustrative and not restrictive. Those skilled in the art will appreciate that changes may be made to these embodiments without departing from the principles and spirit of the invention. Accordingly, the scope of the invention is defined by the appended claims rather than by the description preceding them, and all changes that fall within the metes and bounds of the claims, or equivalents of such metes and bounds thereof, are therefore intended to be embraced by the claims.

The invention claimed is:

1. A method for assessing an imaged subject, the method comprising the steps of:
    obtaining imaging data of said imaged subject, said imaging data being representative of an extensional feature of said imaged subject;
    applying direct quantitative analysis to said imaging data to determine at least one parameter value of said extensional feature, and
    generating an output signal representative of the determined parameter value of said extensional feature;
    the step of applying quantitative analysis further comprising the steps of selecting an imaging data set corresponding to a selected region of said imaged subject, identifying a spatially varying function, that is representative of the cross section of extensional feature in said imaging data set, the spatially varying function comprising non-circular functions and families of profiles, said profiles comprising Gaussian functions and ellipsoid functions and generating said at least one parameter value from the identified spatially varying function.

2. The method of claim 1 wherein the step of identifying a spatially varying function that is representative of the selected imaging data set further comprises the step of profile fitting the selected imaging data set with respective ones of spatially varying functions.

3. The method of claim 2 wherein the step of profile fitting further comprises coincidence fitting pixel brightness data in said selected imaging data with a selected one of said spatially varying functions and determining a best fit profile.

4. The method of claim 1 wherein the step of generating said at least one parameter value from the identified spatially varying function comprises determining the area encompassed by the identified spatially varying function.

5. The method of claim 4 wherein said imaged subject comprises an animal or human body and said extension feature comprises a vessel within said body.

6. The method of claim 5 wherein said at least one parameter value comprises the cross-sectional area of said vessel.

7. The method of claim 5 wherein the selected imaging data set represents a view of said imaged subject selected from the group of views orthogonal to the longitudinal axis of said vessel and views oblique to the longitudinal axis of said vessel.

8. The method of claim 1 further comprising the step of iteratively applying said quantitative analysis to respective selected imaging data sets so as to generate a plurality of respective parameter values for said imaging data sets.

9. The method of claim 1 further comprising the step of preprocessing said image data so as to enhance the contrast between the extensional feature and other portions of said imaging data.

10. The method of claim 1 further comprising the steps of computing background estimates and applying said background estimates in determination of said at least one parameter value.

11. The method of claim 1 wherein the step of obtaining imaging data comprises methods of generating imaging data selected from the groups of tomographic radiography, computed tomography imaging, and magnetic resonance imaging.

12. A method for determining the lumen in a vessel in a body, the method comprising the steps of:
    obtaining imaging data of said vessel comprising a plurality of imaging data sets representative of respective imaging slices through said vessel;
    determining a three-dimensional representation of the longitudinal axis of said vessel;
    computing an orthogonal cross section data set for each of a plurality of respective positions along said longitudinal axis of said vessel;
    wherein the step of determining a three-dimensional representation of the longitudinal axis of said vessel further comprises the steps of computing the lumen center point in selected ones of said imaging slices, wherein computing the lumen center point further comprises generating a mask for a region of interest encompassing said vessel;
    computing a lumen area for each of said respective orthogonal cross section data sets; and
    generating respective signals representative of said lumen areas associated with points along said longitudinal axis.

13. The method of claim 12 wherein the step of generating a mask for said region of interest comprises the steps of determining a seed pixel, performing threshold segmentation, and performing dilation operations.

14. The method of claim 13 wherein the step of computing the lumen center further comprises the step of performing a moment calculation on the binary representation of the bessel cross section provided by said mask.

15. The method of claim 12 wherein the step determining a three-dimensional representation of the longitudinal axis of said bessel further comprises fitting a three-dimensional curve to said plurality of successive lumen center points.

16. The method of claim 12 wherein the step of fitting a three dimensional curve comprises fitting a curve using least mean squared error metrics.

17. The method of claim 12 wherein the step computing a lumen area further comprises the steps of applying direct quantitative analysis to said orthogonal cross-sectional data set to determine said area;
    the step of applying quantitative analysis further comprising the steps of identifying a spatially varying function that is representative of the cross section of said lumen in said orthogonal cross-section data.

18. The method of claim 17 wherein the said spatially varying functions comprise non-circular functions.

19. The method of claim 18 wherein said spatially varying functions comprise families of profiles, said profiles comprising Gaussian functions and ellipsoid functions.

20. The method of claim 17 wherein the step of identifying a spatially varying function that is representative of the cross section of said lumen further comprises the step of profile fitting the orthogonal cross-section data with respective ones of said spatially varying functions.

21. The method of claim 12 wherein said vessel is a blood vessel and said lumen area provides a representation of stenosis in said blood vessel.

* * * * *

UNITED STATES PATENT AND TRADEMARK OFFICE
CERTIFICATE OF CORRECTION

PATENT NO. : 7,333,648 B2
APPLICATION NO. : 10/862101
DATED : February 19, 2008
INVENTOR(S) : Edic et al.

It is certified that error appears in the above-identified patent and that said Letters Patent is hereby corrected as shown below:

Column 13, Line 51, delete "$a^0+a_1x$" and insert -- $a_0+a_1x$ --, therefor.

Column 22, Line 19, delete "AL" and insert -- $A_L$ --, therefor.

Column 36, Line 33, in Claim 14, delete "bessel" and insert -- vessel --, therefor.

Column 36, Line 36, in Claim 15, delete "bessel" and insert -- vessel --, therefor.

Signed and Sealed this

Eleventh Day of November, 2008

JON W. DUDAS
*Director of the United States Patent and Trademark Office*